US008815974B2

(12) United States Patent
Matsushige et al.

(10) Patent No.: US 8,815,974 B2
(45) Date of Patent: Aug. 26, 2014

(54) DENTAL ADHESIVE COMPOSITION

(75) Inventors: Koji Matsushige, Tokyo (JP); Qian Cui, Tokyo (JP); Ayumi Dodomi, Tokyo (JP)

(73) Assignee: Tokuyama Dental Corporation, Tokyo (JP)

( * ) Notice: Subject to any disclaimer, the term of this patent is extended or adjusted under 35 U.S.C. 154(b) by 38 days.

(21) Appl. No.: 13/511,952

(22) PCT Filed: Dec. 2, 2010

(86) PCT No.: PCT/JP2010/071597
§ 371 (c)(1),
(2), (4) Date: May 24, 2012

(87) PCT Pub. No.: WO2011/068164
PCT Pub. Date: Jun. 9, 2011

(65) Prior Publication Data
US 2012/0238658 A1 Sep. 20, 2012

(30) Foreign Application Priority Data
Dec. 4, 2009 (JP) ................. 2009-276046

(51) Int. Cl.
*A61K 6/083* (2006.01)
*A61K 6/00* (2006.01)

(52) U.S. Cl.
CPC .................... *A61K 6/0023* (2013.01)
USPC .......... 523/116; 523/115; 523/113; 523/118; 523/28

(58) Field of Classification Search
None
See application file for complete search history.

(56) References Cited

U.S. PATENT DOCUMENTS

| | | | |
|---|---|---|---|
| 4,259,075 A | 3/1981 | Yamauchi et al. | |
| 4,259,117 A | 3/1981 | Yamauchi et al. | |
| 4,368,043 A | 1/1983 | Yamauchi et al. | |
| 4,539,382 A | 9/1985 | Omura et al. | |
| 4,612,384 A | 9/1986 | Omura et al. | |
| 4,650,847 A | 3/1987 | Omura et al. | |
| 5,295,690 A * | 3/1994 | Johnson ................ | 473/212 |
| 5,556,897 A | 9/1996 | Honda et al. | |
| 6,528,555 B1 | 3/2003 | Nikutowski et al. | |
| 6,583,197 B1 | 6/2003 | Wada et al. | |
| 6,960,079 B2 | 11/2005 | Brennan et al. | |
| 8,357,731 B2 * | 1/2013 | Matsushige et al. ...... | 522/79 |
| 2004/0254261 A1 | 12/2004 | Kojima et al. | |
| 2009/0076189 A1 | 3/2009 | Matsushige et al. | |
| 2010/0216907 A1 * | 8/2010 | Matsushige et al. ........ | 522/154 |
| 2010/0261144 A1 | 10/2010 | Fujinami et al. | |
| 2010/0317762 A1 * | 12/2010 | Matsushige et al. ........ | 523/118 |

FOREIGN PATENT DOCUMENTS

| | | | | |
|---|---|---|---|---|
| EP | 0363903 | | 4/1990 | |
| EP | 363903 A2 * | | 4/1990 | ............... A61K 6/00 |
| EP | 0712622 | | 5/1996 | |
| EP | 712622 A1 * | | 5/1996 | ............... A61K 6/00 |
| EP | 2022463 | | 2/2009 | |
| EP | 2123246 A1 * | | 11/2009 | ............... A61K 6/00 |
| EP | 2305205 | | 4/2011 | |
| JP | 52-113089 | | 9/1977 | |
| JP | 58-21687 | | 2/1983 | |
| JP | 2-157207 | | 6/1990 | |
| JP | 5-85912 | | 4/1993 | |
| JP | 6-9327 | | 1/1994 | |
| JP | 6-24928 | | 2/1994 | |
| JP | 7-82115 | | 3/1995 | |
| JP | 8-319209 | | 12/1996 | |
| JP | 9-263604 | | 10/1997 | |
| JP | 10-236912 | | 9/1998 | |
| JP | 2000-159621 | | 6/2000 | |
| JP | 2001-72523 | | 3/2001 | |
| JP | 2001-122718 | | 5/2001 | |
| JP | 2004-510796 | | 4/2004 | |
| JP | 2004-352698 | | 12/2004 | |
| JP | 2005-529637 | | 10/2005 | |
| WO | 2007/139207 | | 12/2007 | |
| WO | 2008/102489 | | 8/2008 | |
| WO | 2009/051045 | | 4/2009 | |
| WO | 2009/063967 | | 5/2009 | |
| WO | 2010/010901 | | 1/2010 | |

OTHER PUBLICATIONS

International Search Report dated Jan. 18, 2011.
Extended European Search Report dated Dec. 12, 2013 filed in corresponding European patent application No. 10834614.9.

* cited by examiner

*Primary Examiner* — James J Seidleck
*Assistant Examiner* — Peter A Salamon
(74) *Attorney, Agent, or Firm* — Rankin, Hill & Clark LLP

(57) ABSTRACT

[Problems] To provide a liquid dental adhesive composition which contains a phosphoric acid-type compound having a hydrogenphosphoric diester group as an acidic group-containing polymerizable monomer and, further, contains polyvalent metal ions, effectively preventing not only the gelation but also the formation of precipitates (cloudiness) during the storage.
[Means for Solution] A dental adhesive composition which is acidic and contains an acidic group-containing polymerizable monomer (A), polyvalent metal ions (B), water (C), a water-soluble organic solvent (D) and fluoride ions (E), wherein at least 35% by mole of the acidic group-containing polymerizable monomer (A) is a phosphoric acid-type compound having a hydrogenphosphoric diester group, and the contents of the fluoride ions (E) and the polyvalent metal ions (B) are so set that a valence number ratio ($R_F$) defined by the following formula (1):

$$R_F = V_F/TV_P \quad (1)$$

wherein $V_F$ is a valence number of the fluoride ions (E) contained in the composition, and $TV_P$ is a total valence number of the polyvalent metal ions (B) contained in the composition,
satisfies a range of 0.2 to 2.0.

13 Claims, No Drawings

DENTAL ADHESIVE COMPOSITION

TECHNICAL FIELD

This invention relates to a dental adhesive composition for adhering a dental restorative comprising a metal, an organic high molecular material, ceramics or a composite material thereof to a tooth in the field of dental therapy.

BACKGROUND ART

When a tooth is damaged due to decaying and when a cavity is still relatively small, the tooth is directly restored by using a composite resin from the standpoint of aesthetic appearance, simplicity and quickness of operation. When the cavity is relatively large, on the other hand, the cavity is indirectly restored by using a prosthetic material prepared by using a metal, ceramics or a cured resin material.

The dental restorative such as a composite resin or a prosthetic material has no adhesiveness to the tooth. Therefore, the restorative is adhered to the tooth by using an adhesive which comprises a polymerizable composition (usually, a methacrylate-type monomer is a chief component). However, its adhering force to the tooth is not sufficient. For example, when the composite resin is used, the adhering strength that is obtained is not large enough to overcome the internal stress (tensile stress occurring in the interface between the tooth and the composite resin) that generates when the composite resin cures. In many cases, further, the adhering strength is not large enough to withstand the force produced by occlusion.

In order to improve the adhering strength of the adhesive, therefore, the tooth surface is pretreated in two steps, such as:
(a) a hard tooth (enamel comprising chiefly hydroxyapatite) is etched, and
(b) an adhesiveness-improving component called primer is permeated into the tooth,
at the time of using the adhesive.

Here, an aqueous solution of acid is usually used as a pretreating agent (pretreating agent for etching) of (a) above. Concretely, an aqueous solution of phosphoric acid, citric acid or maleic acid is used. Due to the treatment, the tooth is delimed, roughened, and the enamel or the dentin composed of spongy collagen fiber is exposed on the surface of the tooth.

To maintain a sufficiently large adhering strength, however, the adhesive component must permeate through the enamel exposed on the surface to enter into the dentin to a sufficient degree. For this purpose, the pretreatment (treatment with the primer) of (b) above is conducted. As the pretreating material (primer), there has been used an organic solvent of a hydrophilic monomer having excellent affinity to the tooth, such as hydroxyethyl methacrylate (HEMA) or the like. The primer by itself does not usually contain any polymerization initiator. However, the polymerizable monomer contained in the primer is polymerized and cured by the action of radicals formed by the adhesive at the time when the adhesive applied onto the primer undergoes the photo-curing reaction.

While the pretreatment is conducted as described above, there have been developed various dental adhesive compositions containing a polymerizable monomer having adhesiveness to the tooth in order to attain higher adhering strength and to reduce complexity of pretreating operation.

For example, a patent document 1 and a patent document 2 are proposing dental adhesive compositions containing an acidic group-containing polymerizable monomer as at least part of the polymerizable monomer component. These adhesive compositions exhibit higher adhering strengths since the acidic group-containing polymerizable monomer having an acidic group such as phosphoric acid group or carboxylic acid group in the molecules thereof exhibits a high affinity to the tooth (hydroxyapatite or collagen).

Further, patent documents 3 to 6 are proposing adhesive compositions in which an acidic group-containing polymerizable monomer is present together with water. These adhesive compositions exhibit both the etching function of the acid aqueous solution and the primer permeation accelerating function of the primer, and eliminate the need of separately applying a pretreating agent. Namely, these adhesive compositions can be used upon being applied only once, and can be advantageously used as adhesives (one-step type adhesives) featuring excellent operability. Further, the adhesive compositions containing the acidic group-containing polymerizable monomer and water can be used not only as adhesives but also as self-etching primers having the above-mentioned etching function and the permeation accelerating function (e.g., see patent document 7 and patent document 8).

As adhesives and self-etching primers having higher adhering strengths, there have, further, been known liquid adhesive compositions containing polyvalent metal ions obtained by being further blended with polyvalent metal ion-eluting fillers in addition to the acidic group-containing polymerizable monomer and water (e.g., see patent document 9 and patent document 10). Namely, with these adhesive compositions, not only the polymerizable monomer containing the acidic group-containing polymerizable monomer simply polymerizes but also the polyvalent metal ions ionically bond to the acidic groups of the acidic group-containing polymerizable monomer to form a reinforced structure. It is, therefore, presumed that the mechanical strength of the cured body is greatly enhanced.

Here, as the polyvalent metal ions, there can be exemplified alkaline earth metal ions and aluminum ions. As preferred acidic group-containing polymerizable monomers, further, there have been known those of the phosphoric acid type having an acidic group for their high acidity and strong affinity to the tooth. Among them, a polymerizable monomer having a hydrogenphosphoric diester group, such as bis(2-methacryyloyloxyethyl) hydrogenphosphate, is difunctional imparting not only a high acidity and affinity to the tooth but also imparting a crosslinked structure due to the chemical bond to the cured body making it possible to further improve the mechanical strength of the cured body, and is most desired. The difunctional polymerizable monomer having the hydrogenphosphoric diester group is, usually, used being mixed with a monofunctional acidic group-containing polymerizable monomer ((2-methacryloyloxyethyl)hydrogenphosphate, etc.)

PRIOR ART DOCUMENTS

Patent Documents

Patent document 1: JP-A-52-113089
Patent document 2: JP-A-58-21687
Patent document 3: JP-A-2004-352698
Patent document 4: JP-A-9-263604
Patent document 5: JP-A-10-236912
Patent document 6: JP-A-2001-72523
Patent document 7: JP-A-7-82115
Patent document 8: JP-A-2000-159621

Patent document 9: pamphlet of International Publication WO2007/139207

Patent document 10: pamphlet of International Publication WO2008/102489

OUTLINE OF THE INVENTION

Problems that the Invention is to Solve

However, a problem arouses in the storage stability if the above-mentioned liquid adhesive compositions containing polyvalent metal ions are blended with a large amount of the acidic group-containing polymerizable monomer having a hydrogenphosphoric diester group to increase the adhering force. Namely, with these adhesive compositions, the ionic bond forms between the multivalent metal ions and the acidic group-containing polymerizable monomer during the storage. The ionic bond that occurs to a suitable degree works to improve the applicability and is favorable for attaining the adhering strength. If occurs to an excess degree, however, the ionic bond rather lowers the adhering strength and finally causes the liquid adhesive compositions to be gelled so that they cannot be used (applied).

In order to effectively suppress the problem of gelling, therefore, the patent documents 9 and 10 teach diluting the acidic group-containing polymerizable monomer and the concentration of the polyvalent metal ions by adding a water-soluble organic solvent thereto so as to satisfy predetermined conditions so that the ionic bond occurs within only a suitable range while the adhesive composition is being stored. Here, the adhesive composition can be prevented from being gelled when the phosphoric acid-type compound having a hydrogenphosphoric diester group is used as the acidic group-containing polymerizable monomer accompanied, however, by a specific problem in that the liquid adhesive composition becomes cloudy.

That is, the cloudiness is caused by the precipitation of a white composition insoluble in the water-soluble organic solvent while the liquid adhesive composition is being stored. The cloudiness spoils the appearance, lowers the commercial value of the adhesive composition, causes the amount of the polyvalent metal ions to become insufficient in the composition, and decreases the adhering strength. Further, the liquid adhesive composition is, usually, stored being contained in a dropping bottle and, at the time of use, is applied being discharged from the liquid discharge nozzle of the dropping bottle. If the cloudiness is taking place, however, the liquid discharge nozzle is often clogged, and improvement is awaited.

It is, therefore, an object of the present invention to provide a liquid dental adhesive composition which contains a phosphoric acid-type compound having a hydrogenphosphoric diester group as a acidic group-containing polymerizable monomer and, further, contains polyvalent metal ions, effectively preventing not only the gelation but also the formation of precipitates (cloudiness) during the storage.

Means for Solving the Problems

The present inventors have keenly forwarded the study concerning the dental adhesive compositions containing the phosphoric acid-type compound and polyvalent metal ions, have discovered that the problems of gelation and cloudiness during the storage can be effectively solved by making present a specific amount of fluoride ions together with the polyvalent metal ions, and have completed the invention.

According to the present invention, there is provided a dental adhesive composition which is acidic and contains an acidic group-containing polymerizable monomer (A), polyvalent metal ions (B), water (C), a water-soluble organic solvent (D) and fluoride ions (E), wherein at least 35% by mole of the acidic group-containing polymerizable monomer (A) is a phosphoric acid-type compound having a hydrogenphosphoric diester group; and the contents of the fluoride ions (E) and the polyvalent metal ions (B) are so set that a valence number ratio ($R_F$) defined by the following formula (1):

$$R_F = V_F / TV_P \qquad (1)$$

Wherein, $V_F$ is a valence number of the fluoride ions (E) contained in the composition, and $TV_P$ is a total valence number of the polyvalent metal ions (B) contained in the composition, satisfies a range of 0.2 to 2.0.

In the dental adhesive composition of the present invention, the following embodiments are preferably employed:

1. The contents of the polyvalent metal ions (B) and the acidic group-containing polymerizable monomer (A) are so set that the valence number ratio ($R_P$) defined by the following formula (2):

$$R_P = TV_P / TV_A \qquad (2)$$

Wherein, $TV_P$ is a total valence number of the polyvalent metal ions (B) contained in the composition, and $TV_A$ is a total valence number of the acidic groups possessed by the acidic group-containing polymerizable monomer (A) contained in the composition, satisfies a range of 0.1 to 1.5;

2. The phosphoric acid-type compound having the hydrogenphosphoric diester group is a bis[2-(meth)acryloyloxyethyl] hydrogenphosphate;

3. The acidic group-containing polymerizable monomer (A) is partly a phosphoric acid-type compound having a dihydrogenphosphoric monoester group;

4. The phosphoric acid-type compound having the dihydrogenphosphoric monoester group is a 2-(meth)acryloyloxyethyl dihydrogenphosphate;

5. The dental adhesive composition, further, contains a non-acidic polymerizable monomer (F) which has no acidic group;

6. The content of water (C) is 10 to 120 parts by mass per 100 parts by mass of the acidic group-containing polymerizable monomer (A);

7. The content of the water-soluble organic solvent (D) is 100 to 600 parts by mass per 100 parts by mass of the acidic group-containing polymerizable monomer (A);

8. The content of the non-acidic polymerizable monomer (F) is not more than 500 parts by mass per 100 parts by mass of the acidic group-containing polymerizable monomer (A);

9. The dental adhesive composition, further, contains an effective amount of a photopolymerization initiator (G) and is used as a dental adhesive; and 10. The dental adhesive composition is used as a tooth-pretreating material prior to applying the dental adhesive.

According to the present invention, there is further provided a method of producing a dental adhesive composition which contains an acidic group-containing polymerizable monomer (A), polyvalent metal ions (B), water (C), a water-soluble organic solvent (D) and fluoride ions (E), comprising:

using a phosphoric acid-type compound having a hydrogenphosphoric diester group as at least 35% by mole of the acidic group-containing polymerizable monomer (A);

using a polyvalent metal ion-releasing component (B') as a source of the polyvalent metal ions (B);

using a fluoride ion-releasing component (E') as a source of the fluoride ions (E);

mixing the acidic group-containing polymerizable monomer (A), polyvalent metal ion-releasing component (B'), water (C), water-soluble organic solvent (D) and fluoride ion-releasing component (E') together, and ripening the mixture so that the polyvalent metal ions and the fluoride ions released from the polyvalent metal ion-releasing component (B') and the fluoride ion-releasing component (E') maintain a valence number ratio ($R_F$) represented by the following formula (1), $$R_F = V_F / TV_P \qquad (1)$$

Wherein, $V_F$ is a valence number of the fluoride ions (E) contained in the composition, and $TV_P$ is a total valence number of the polyvalent metal ions (B) contained in the composition, that lies a range of 0.2 to 2.0.

In the method of production of the invention, either the polyvalent metal ion-releasing component (B') or the fluoride ion-releasing component (E') may be a multi-ion-releasing component (B'E') which releases the polyvalent metal ions and the fluoride ions.

Effects of the Invention

The dental adhesive composition of the invention contains, as an acidic group-containing polymerizable monomer component, a polymerizable monomer having a hydrogenphosphoric diester group having a high deliming action and affinity to the tooth at a high concentration (not less than 35% by mol) and, further, contains polyvalent metal ions. Therefore, if the composition is cured, the obtained cured body forms a reinforced structure based on the ionic bond of the polyvalent metal ions to the acidic groups of the acidic group-containing polymerizable monomer, and exhibits a high adhering strength to the tooth. Specifically, when the phosphoric acid-type compound having a hydrogenphosphoric diester group used as the acidic group-containing polymerizable monomer (A), is a bis(2-methacryloyloxyethyl)hydrogenphosphate, the adhesion to the tooth is further improved.

The dental adhesive composition of the invention is a liquid and can be stored in one package with all components being mixed therein. In this form of storage, the dental adhesive composition is not gelled, does not become cloudy (does not form white precipitate insoluble in the solvent), does not cause a decrease in the adhering strength due to cloudiness or in the appearance, and effectively prevents a decrease in the applicability, i.e., prevents clogging in the liquid discharge nozzle of the dropping bottle.

For example, in the conventional dental adhesive composition of the one-package type, when the polymerizable monomer and the polyvalent metal ions were contained therein, the gelation could be suppressed even after stored for extended periods of time. When the polymerizable monomer having the hydrogenphosphoric diester group as the acidic group was used, however, formation of the cloudiness (i.e., white precipitation insoluble in the solvent) could not be suppressed, and the cloudiness caused a decrease in the adhering strength, appearance and applicability. The present invention now effectively prevents such inconveniences.

MODE FOR CARRYING OUT THE INVENTION

The dental adhesive composition of the present invention contains, as basic components, an acidic group-containing polymerizable monomer (A), polyvalent metal ions (B), water (C), a water-soluble organic solvent (D) and fluoride ions (E), and may, further, contain monovalent metal ions in addition to the component (B) and the component (E). As required, the dental adhesive composition may, further, contain a non-acidic polymerizable monomer (F) and a photopolymerization initiator (G), and may, further, contain a variety of blending agents that have been known in the field of dentistry.

<Acidic Group-Containing Polymerizable Monomers (A)>

The acidic group-containing polymerizable monomer (A) used in the invention is a component which when cured by polymerization works to impart adhesiveness to the composite resin or to various prosthetic materials, and has, in the molecules thereof, a polymerizable group (polymerizable unsaturated group) as well as an acidic group for forming ionic crosslinking with the polyvalent metal ions (B) as will be described later.

As the polymerizable unsaturated group, there can be exemplified acryloyl group, methacryloyl group, acrylamide group, methacrylamide group, vinyl group, allyl group, ethynyl group and styryl group. From the standpoint of curing rate, in particular, it is desired to use acryloyl group, methacryloyl group, acrylamide group or methacrylamide group. Most desirably, acryloyl group or methacryloyl group is used.

(A-1) Polymerizable Monomers Having a Hydrogenphosphoric Diester Group

In the invention, it is necessary to use a phosphoric acid-type compound having a hydrogenphosphoric diester group as an acid group (hereinafter simply called phosphoric diester monomer) as not less than 35% by mole of the acid group-containing polymerizable monomer (A).

The hydrogenphosphoric diester group is represented by the following formula,

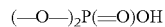

and the phosphoric diester monomer (A-1) having an acidic group derived from the phosphoric acid exhibits not only a high deliming action for the tooth but also a large bonding force to the tooth. The hydrogenphosphoric diester group, further, has two hydrocarbon groups bonded by ester bond. Therefore, when either of these hydrocarbon groups has a polymerizable unsaturated group, the monomer (A-1) is difunctional, and imparts a crosslinked structure based on the chemical bond to the cured body to further increase the adhering strength. With the polymerizable monomer having an acidic group derived from the phosphoric acid (e.g., having an acidic group such as phosphinic acid group, phosphoric acid group, hydrogenphosphonic monoester group, dihydrogenphosphoric monoester, etc. which are other than the hydrogenphosphoric diester group), the adhering strength that is obtained is not so large as that obtained by using the polymerizable monomer (A-1) that has the hydrogenphosphoric diester group.

If the phosphoric diester monomer (A-1) having the hydrogenphosphoric diester group as the acidic group is used in large amounts, the adhering strength to the tooth can be increased accompanied, however, by a specific problem of formation of white precipitation (cloudiness) insoluble in the solvent due to the use of the polymerizable monomer (A-1).

In the present invention, therefore, it is desired to use the phosphoric diester monomer (A-1) in an amount of 35 to 60% by mole, specifically, 40 to 60% by mole and, most desirably, 45 to 50% by mole in order to increase the adhering strength while preventing the cloudiness.

In the invention, a difunctional monomer or a monofunctional monomer represented by the following general formulas can be preferably used as the phosphoric diester monomer (A-1).

Here, in the following formulas, $R^1$ is a hydrogen atom or a methyl group, and n and m are, independently from each other, integers of 1 to 10.

Difunctional Monomer:

[Chemical 1]

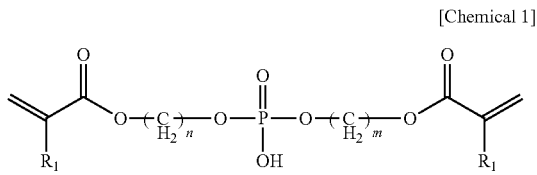

Monofunctional Monomer:

[Chemical 2]

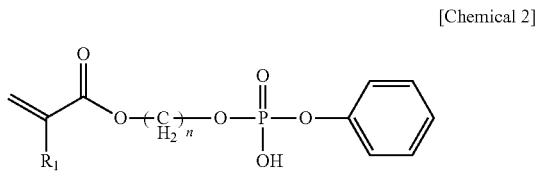

The following compounds are concrete examples of the phosphoric diester monomer (A-1) which is the difunctional monomer represented by the above general formula:
bis[2-(meth)acryloyloxyethyl] hydrogenphosphate,
bis[2-(meth)acryloyloxyhexyl] hydrogenphosphate,
bis[2-(meth)acryloyloxydecyl] hydrogenphosphate, and
2-(meth)acryloyloxyethyl 2'-(meth)acryloyloxyhexyl hydrogenphosphate.

The following compounds are concrete examples of the phosphoric diester monomer (A-1) which is the monofunctional monomer represented by the above general formula:
2-(meth)acryloyloxyethylphenyl hydrogenphosphate, and
6-(meth)acryloyloxyhexylphenyl hydrogenphosphate.

In addition to the above difunctional or monofunctional monomers, there can be further used the following compounds as the phosphoric diester monomer (A-1):
3-di(meth)acryloylpropane-2-phenyl hydrogenphosphate, and
bis[5-{2-(meth)acryloyloxyethoxycarbonyl}heptyl] hydrogenphosphate.

In the invention, the above-exemplified phosphoric diester monomers (A-1) can be used alone or in a mixture of two or more kinds. Among them, the difunctional monomer is preferred because of the reasons mentioned above. From the standpoint of more distinctly suppressing the formation of precipitate, it is more desired to use a bilaterally symmetrical compound which is the difunctional monomer represented by the above general formula in which n and m are the same integers.

In the invention, the most preferred phosphoric diester monomer (A-1) is a bis[2-(meth)acryloyloxyethyl] hydrogenphosphate.

(A-2) Other Acidic Group-Containing Polymerizable Monomers.

The dental adhesive composition of the present invention may contain other acidic group-containing polymerizable monomers (A-2) so far as the predetermined ratio of the acidic group-containing polymerizable monomer (A) comprises the above-mentioned phosphoric diester monomer (A-1). The acidic group possessed by the polymerizable monomers (A-2) can be represented by a dihydrogenphosphoric monoester group, i.e., by a group of the following formula,

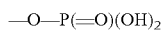

As the polymerizable monomer having the dihydrogen phosphoric monoester group, there can be exemplified the following compounds:
2-(meth)acryloyloxyethyl dihydrogenphosphate,
4-(meth)acryloyloxybutyl dihydrogenphosphate,
6-(meth)acryloyloxyhexyl dihydrogenphosphate,
10-(meth)acryloyloxydecyl dihydrogenphosphate, and
1,3-di(meth)acryloylpropane-2 dihydrogenphosphate.

Among these compounds, the 2-(meth)acryloyloxyethyl dihydrogenphosphate is most desired.

As acidic groups other than the dihydrogenphosphoric monoester group, there can be exemplified:
carboxyl group (—COOH),
sulfonic acid group (—SO$_3$H),
phosphinico group {>P(=O)OH},
acid anhydride group {(—CO)$_2$O}, and
acid halide group (—COX).

As the polymerizable monomer having the above acid group, there can be exemplified the following compounds.

Compounds Having a Carboxyl Group as the Acidic Group:
(meth)acrylic acid,
N-(meth)acryloylglycine,
N-(meth)acryloylaspartic acid,
N-(meth)acryloyl-5-aminosalicylic acid,
2-(meth)acryloyloxyethyl hydrogensuccinate, and
2-(meth)acryloyloxyethyl hydrogenphthalate.

Compounds Having a Plurality of Carboxyl Groups as Acidic Groups:
11-(meth)acryloyloxyundecane-1,1-dicarboxylic acid,
10-(meth)acryloyloxydecane-1,1-dicarboxylic acid,
12-(meth)acryloyloxydodecane-1,1-dicarboxylic acid,
4-(meth)acryloyloxybutyl trimellitate,
4-(meth)acryloyloxyhexyl trimellitate, and
4-(meth)acryloyloxydecyl trimellitate.

Compounds Having the Phosphinico Group as an Acidic Group:
vinylphosphonic acid, and
p-vinylbenzenephosphonic acid.

Compounds Having the Sulfonic Acid Group as an Acidic Group:
2-(meth)acrylamide-2-methylpropanesulfonic acid,
p-vinylbenzenesulfonic acid, and
vinylsulfonic acid.

Further, the acid anhydrides and acid halides derived from the compounds having one or a plurality of the above-exemplified carboxyl groups, can also be used as the other acidic group-containing polymerizable monomers (A-2).

Among the above other acidic groups according to the present invention, the dihydrogenphosphoric monoester group is, particularly, desired and it is most desired to use the compound having the above acidic group as the other polymerizable monomer (A-2) in combination with the phosphoric diester monomer (A-1).

That is, like the phosphoric diester group, the dihydrogenphosphoric monoester group is an acidic group of the phosphoric acid-type which highly adheres to the tooth. Besides, the other monomer (A-2) having the dihydrogenphosphoric monoester group is formed as a by-product at the time of producing the phosphoric diester monomer (A-1), and can, therefore, be obtained as a mixture with the phosphoric diester monomer (A-1). Moreover, the dihydrogenphosphoric monoester group is a divalent acidic group, and has reaction points at two places so as to ionically bond to the polyvalent metal ions that will be described later. Therefore, the reinforcing structure due to the ionic bond becomes more dense.

In the present invention, therefore, it is most desired to use, as the acidic group-containing polymerizable monomer (A), a mixture of the phosphoric diester monomer (A-1) and the monomer (A-2) having the dihydrogenphosphoric monoester group from such a standpoint that a further improved adhering strength is obtained from the reinforcing effect of the ionic bond of the monomer (A-2) having the dihydrogenphosphoric monoester group and the reinforcing effect of the chemical bond of the phosphoric diester monomer (A-1).

<Polyvalent Metal Ions (B)>

In the present invention, it is important that the phosphoric diester monomer (A-1) contained in the above-mentioned acidic group-containing polymerizable monomer (A) is present together with the polyvalent metal ions (B). With the polyvalent metal ions (B) being present together with the phosphoric diester polymerizable monomer (A-1), the reinforced structure due to the ionic bond develops to a sufficient degree and a large adhering strength is obtained.

The polyvalent metal ions (B) are metal ions having a valence of 2 or more which can be ionically bonded to acidic groups (e.g., hydrogenphosphoric diester groups) possessed by the acidic group-containing polymerizable monomer (A), and may be any polyvalent metal ions so far as they can be bonded to the acidic groups. Their concrete examples include the following ions of divalent metals or trivalent metals.

Divalent Metals:
magnesium, calcium, strontium, barium, zinc, copper (II), tin (II), etc.

Trivalent Metals:
aluminum, gallium, indium, scandium, yttrium, lanthanum, cerium, praseodymium, promethium, neodymium, samarium, europium, gadolinium, terbium, dysprosium, holmium, erbium, thulium, ytterbium, iron (III), actinium, etc.

In the invention, among the ions of the above-exemplified polyvalent metals, the ions of the trivalent metals are preferred from the standpoint of adhering strength. Specifically, it is desired that not less than 60% by mole of the whole polyvalent metal ions (B) are trivalent metal ions.

Among the above-exemplified trivalent metal ions, further, specifically desired are earth metal ions, i.e., ions of metals belonging to the Group 3 and Group 13 of periodic table. Concretely, aluminum ions or ions of rare earth metals such as yttrium, scandium and lanthanoide are preferred. Among them, aluminum ions and lanthanum ions are most desired.

Though there is no specific limitation on the amount of the polyvalent metal ions (B) present in the adhesive composition of the invention, it is desired that a total valence number ratio ($R_P$) defined by the following formula (2), $$R_P = TV_P/TV_A \quad (2)$$

Wherein,
$TV_P$ is a total valence number of the polyvalent metal ions (B) contained in the composition, and
$TV_A$ is a total valence number of the acidic groups possessed by the acidic group-containing polymerizable monomer (A) contained in the composition,
lies in a range of 0.1 to 1.5 and, specifically, 0.2 to 0.9.

In the formula (2) representing the total valence number ratio ($R_P$), the total valence number ($TV_A$) of the acidic groups possessed by the acidic group-containing polymerizable monomer (A) contained in the adhesive composition is calculated according to the following formula (2a), $$TV_A = \Sigma P_k \times A_k \quad (2a)$$

Wherein,
k is 1, 2, 3, - - - , n,
n is a number of the kinds of the acidic group-containing polymerizable monomers contained in the composition,
$P_k$ is a mol number of each of the acidic group-containing polymerizable monomers contained in the composition, and
$A_k$ is a valence number of the acidic group possessed by each of the acidic group-containing polymerizable monomers.

For example, the hydrogenphosphoric diester monomer (A-1) such as bis[2-(meth)acryloyloxyethyl] hydrogenphosphate has an acidic group of a valence number of 1. The dihydrogenphosphoric monoester monomer (A-2) such as 2-(meth)acryloyloxyethyl dihydrogenphosphate has an acidic group of a valence number of 2.

When the acidic group-containing polymerizable monomer (A) contained in the adhesive composition consists of only one kind of the phosphoric diester monomer (A-1), the valence number calculated for the phosphoric diester monomer (A-1) according to the above formula (2a) becomes the total valence number ($TV_A$). When the composition contains a plurality of kinds of acidic group-containing polymerizable monomers inclusive of the phosphoric diester polymerizable monomer, the valence numbers are calculated for each of the acidic group-containing polymerizable monomers, and the total value thereof becomes the total valence number ($TV_A$).

On the other hand, the total valence number ($TV_P$) of the polyvalent metal ions (B) contained in the composition is calculated according to the following formula (2b), $$TV_P = \Sigma I_k \times B_k \quad (2b)$$

Wherein,
k is 1, 2, 3, - - - , n,
n is a number of the kinds of the metal ions contained in the composition,
$I_k$ is a mol number of each of the respective kinds of the polyvalent metal ions contained in the composition, and
$B_k$ is a valence number of each of the respective kinds of the polyvalent metal ions.

The kind and content of the polyvalent metal ions (B) present in the dental adhesive composition of the invention can be found by taking measurement by using an inductively coupled plasma (ICP) emission spectroscopy after the solid components have been removed. Concretely, the adhesive composition is diluted with a water-soluble organic solvent down to a concentration of 1% by mass, and the obtained diluted solution is filtered by using a syringe filter to remove the solid components. Next, the ion species and the ion concentration of the obtained filtrate are measured by using the ICP emission spectroscopy to calculate the ion species of the polyvalent metals and the amounts thereof in the adhesive composition.

As for the kind and content of the acidic group possessed by the acidic group-containing polymerizable monomer (A) in the dental adhesive composition, each acidic group-containing polymerizable monomer is isolated from the composition by using a high-performance liquid chromatography for separation, the molecular weight thereof is measured from the analysis of mass of each acidic group-containing polymerizable monomer, and the structure thereof is determined by the nuclear magnetic resonance spectroscopy (NMR) to thereby identify the acidic group and to calculate the content thereof.

For example, upon taking $^{31}$P-NMR measurement, the hydrogenphosphoric diester group can be identified from the chemically shifted value thereof. Namely, by using a known compound having a hydrogenphosphoric diester group or, concretely, by using the dimethyl hydrogenphosphate as a standard substance, the standard substance is measured by $^{31}$P-NMR under the same conditions (diluting solvent, concentration, temperature) and is compared with the $^{31}$P-NMR measured for the adhesive composition to determine the chemically shifted value.

Here, the monomethyl dihydrogenphosphate is used as a standard substance for the polymerizable monomer (A-2) that has the dihydrogenphosphoric monoester group as an acidic group.

The amount of the acidic group-containing polymerizable monomer in the composition can be found by preparing a calibration curve of the monomers isolated by the high-performance liquid chromatography for separation and the standard substance, adding an internal standard substance to part of the filtrate and taking a measurement using the high-performance liquid chromatography.

In the invention as described earlier, it is desired that the amount of the polyvalent metal ions (B) present together with the acidic group-containing polymerizable monomer (A) is so adjusted that the total valence number ratio ($R_P$) represented by the above formula (2) is from 0.1 to 1.5 and, specifically, from 0.2 to 0.9.

That is, part of the polyvalent metal ions (B) present in the adhesive composition form ionic bond with the acidic group-containing polymerizable monomer (A); i.e., the polyvalent metal ions (B) are not all ionically bonded. In order for the ionic bond to develop to a sufficient degree, the polyvalent metal ions (B) must be present maintaining a predetermined balance relative to the acidic groups possessed by the acidic group-containing polymerizable monomer (A).

For example, if the polyvalent metal ions (B) are present in an amount smaller than the amount of the acidic group-containing polymerizable monomer (A) and if the total valence number ratio ($R_P$) is smaller than the above-mentioned range, then the ionic bond does not develop to a sufficient degree and a large adhering strength cannot be obtained.

Further, if the amount of the polyvalent metal ions (B) is larger than that of the acidic group-containing polymerizable monomer (A) and if the total valence number ratio ($R_P$) is larger than the above-mentioned range, then the amount of the acidic groups is so small that the ionic bond does not develop to a sufficient degree, either. Besides, gelation easily occurs, deliming action of the acidic group-containing polymerizable monomer (A) decreases, and a large adhering strength is not obtained, either. Further, even if the adhering strength which is large to some extent may be obtained, it is probable that the cured product may lack durability of adhesion. That is, the cured product may lack water-resisting property, and the adhering strength decreases in relatively short periods of time.

In the adhesive composition of the present invention which uses a mixture of a bis[2-(meth)acryloyloxyethyl] hydrogenphosphate (A-1) and a 2-(meth)acryloyloxyethyl dihydrogenphosphate (A-2) as the acid group-containing polymerizable monomer (A) and in which not less than 60% by mole of the polyvalent metal ions (B) are trivalent metal ions, the amount of the polyvalent metal ions (B) is selected to be in a range of 20 to 500 mmols, more preferably, in a range of 30 to 300 mmols and, most preferably, in a range of 50 to 150 mmols per 100 parts by mass of the mixture.

As described already, further, the polyvalent metal ions (B) are desirably trivalent metal ions. It is desired that the total valence number of polyvalent metal ions other than the trivalent metal ions is limited to be not more than 50% and, specifically, not more than 20% of the total valence number of the polyvalent metal ions (B) contained in the adhesive composition. In other words, the total valence number ratio ($R_3$) of the trivalent metal ions (specifically, earth metal ions) to the polyvalent metal ions is represented by the following formula (3), $$R_3 = TV_3/TV_P \qquad (3)$$

Wherein,
  $TV_3$ is a total valence number of the trivalent metal ions contained in the composition, and
  $TV_P$ is a total valence number of the polyvalent metal ions contained in the composition,
and it is desired that the total valence number ratio ($R_3$) is in a range of not less than 0.5 and, specifically, not less than 0.8.

<Water C>

In the present invention, water (C) serves as a solvent for homogeneously dispersing various components therein, and is necessary for deliming the tooth and for promoting the ionic bond between the acidic group-containing polymerizable monomer (A) and the polyvalent metal ions (B).

Water (C) is desirably distilled water or deionized water substantially free of impurities detrimental to storage stability and therapeutic components. After the adhesive composition has been applied to the tooth and the deliming has been effected to a sufficient degree, water (C) is dried by blowing the air and has, usually, been removed at the time of polymerization.

The amount of water (C) is, desirably, 10 to 120 parts by mass and, specifically, 50 to 100 parts by mass per 100 parts by mass of the acidic group-containing polymerizable monomer (A). If the amount of water (C) is smaller than the above range, the tooth is not sufficiently delimed and the ionic bond does not develop sufficiently, and a large adhering strength is not obtained. If water is used in amounts larger than the above range, on the other hand, it becomes difficult to remove water by blowing the air after the adhesive composition has been applied onto the tooth surface; i.e., water remains much on the tooth surface and a sufficiently large adhering strength may not be obtained.

<Water-Soluble Organic Solvent (D)>

In the invention, the water-soluble organic solvent (D) is a so-called diluting solvent which works to prevent the acidic group-containing polymerizable monomer (A) and the polyvalent metal ions (B) from excessively ionically bonded together and to prevent the adhesive composition from increasing its viscosity or from being gelled while the adhesive composition is being stored. That is, upon being blended with the water-soluble organic solvent (D), the adhesive composition can be stored in the state of one liquid (i.e., in the state of one package) blended with all components.

Like water (C), the water-soluble organic solvent (D), too, is dried by blowing the air after the adhesive composition has been applied to the tooth. Upon drying the water-soluble organic solvent (D) and water (C), the acidic group-containing polymerizable monomer (A) and the polyvalent metal ions (B) are condensed and, as a result, the ionic bond is further promoted between the two to attain higher adhesion to the tooth.

Therefore, the water-soluble organic solvent (D) used in the invention must be soluble in water and must, at the same time, be volatile at room temperature.

In this specification, "volatile" means that the boiling point at 760 mmHg is not higher than 100° C. and the vapor pressure at 20° C. is not less than 1.0 KPa. Further, "water-soluble" means that the solubility in water at 20° C. is not less than 20 g/100 ml.

As the volatile water-soluble organic solvent (D), there can be exemplified methanol, ethanol, n-propanol, isopropyl alcohol, acetone and methyl ethyl ketone. As required, a plurality of these organic solvents can be used being mixed together. If toxicity to the living body is taken into consideration, it is desired to use ethanol, isopropyl alcohol or acetone.

The water-soluble organic solvent (D) is used in an amount of, preferably, 100 to 600 parts by mass per 100 parts by mass of the acidic group-containing polymerizable monomer (A) and, more preferably, in an amount of 200 to 500 parts by mass if a balance of adhesion to the tooth and effect for suppressing an increase in the viscosity is taken into consideration. If the amount of use of the water-soluble organic solvent (D) is smaller than this range, the viscosity cannot be suppressed to a sufficient degree, the applicability decreases, and the adhering strength to the tooth tends to decrease. If used in amounts larger than the above range, on the other hand, the water-soluble organic solvent (D) remains on the tooth surface unless it is blown with the air to an excess degree, and a sufficiently large adhering force cannot be obtained. Moreover, since the concentration of the adhesive component tends to become lean, the adhesive component becomes insufficient in the component that remains on the tooth surface after the air-blow treatment, and a sufficiently large adhering strength is not obtained.

<Fluoride Ions (E)>

The greatest feature of the dental adhesive composition of the present invention resides in that the fluoride ions (E) are contained together with the above-mentioned components (A) to (D), the fluoride ions $F^-$ (E) being present in the adhesive composition in such an amount that the valence number ratio ($R_F$) thereof to the total valence number of the polyvalent metal ions (B) being in a range of 0.2 to 2.0 and, specifically, 0.3 to 1.0.

The valence ratio ($R_F$) is defined by the following formula (1), $$R_F = V_F / TV_P \quad (1)$$

Wherein,
$V_F$ is a valence number (mol number) of the fluoride ions contained in the composition, and
$TV_P$ is a total valence number of the polyvalent metal ions (B) contained in the composition as described above.

In the above formula (1), the fluoride ions $F^-$ are monovalent anions and their valence number $V_F$ is equal to the mol number of the fluoride ions $F^-$ contained in the composition. Further, as represented by the above formula (2b), the total valence number $TV_P$ of the polyvalent metal ions (B) is found as the sum of values (integrated values) obtained by multiplying the mol numbers of the respective kinds of the polyvalent metal ions (B) by the ionic valence numbers of the respective kinds of the polyvalent metal ions (B).

The dental adhesive composition of the present invention contains the fluoride ions $F^-$ (E) in such an amount that the valence number ratio ($R_F$) lies in the above-mentioned range and, therefore, highly suppresses the occurrence of white precipitation during the storage despite the hydrogenphosphoric diester monomer (A-1) is used as the acidic group-containing polymerizable monomer (A). Though the reason has not been clarified yet, the present inventors presume that the following action is taking place.

For example, the fluoride ions $F^-$ of the component (E) are part of the plurality of kinds of anions that ionically bond to the polyvalent metal ions (B) together with the acidic groups of the acidic group-containing polymerizable monomer (A), and are taken in by the obtained ionically bonded product (salt) presumably causing the crystallinity of the ionically bonded product (salt) to be lowered. Namely, while the fluoride ions $F^-$ are conjugated base ions of the hydrofluoric acid, the hydrofluoric acid is a relatively strong acid having a pKa value of 3.17. Though their pKa value is larger than the pKa value (2.15) which is based on the first dissociation of the phosphoric diester group, their ionic radius is small accounting for a high degree of ionic bond of the fluoride ions $F^-$ with the polyvalent metal ions (B). Further, if the molecular weight is taken into consideration, a large steric hindrance is caused when the acidic group-containing polymerizable monomer (A) forms a plurality of ionic bonds with the polyvalent metal ions (B).

With the adhesive composition being blended with the predetermined amount of fluoride ions $F^-$, therefore, the ionically bonded product (salt) tends to assume a state where not only the acidic group of the acidic group-containing polymerizable monomer (A) but also at least one fluoride ion $F^-$ are bonded thereto. This lowers the crystallinity of the ionically bonded product (salt) of the acidic group-containing polymerizable monomer (A) and the polyvalent metal ions (B) changing into a structure which permits the ionically bonded product (precipitate) to precipitate less. It is thus presumed that the cloudiness (insoluble white precipitation) is effectively prevented during the storage.

Here, if the amount of the fluoride ions $F^-$ is smaller than the above-mentioned range, the effect for suppressing the precipitation is not sufficiently exhibited during the storage arousing problems of a decrease in the adhering strength and clogging of a liquid discharge nozzle when the composition is contained in a dropping bottle. If the amount of the fluoride ions $F^-$ is larger than the above range, too, the polyvalent metal ions (B) and the acidic group-containing polymerizable monomer (A) fail to be smoothly and ionically bonded together, and the adhering strength to the tooth decreases.

In the invention, there is no specific limitation on the amount of the fluoride ions $F^-$ in the adhesive composition so far as it lies within the above-mentioned range. When the adhesive composition contains a mixture of a bis[2-(meth) acryloyloxyethyl] hydrogenphosphate (A-1) and a 2-(meth) acryloyloxyethyl dihydrogenphosphate (A-2) as the acidic group-containing polymerizable monomer (A) and in which not less than 60% by mole of the polyvalent metal ions (B) are trivalent metal ions, however, it is desired that the amount of the fluoride ions $F^-$ in the adhesive composition is in a range of 20 to 800 mmols, more preferably, 30 to 300 mmols and, most preferably, 50 to 200 mmols per 100 parts by mass of the mixture (i.e., acidic group-containing polymerizable monomer (A)).

In the invention, the amount of the fluoride ions $F^-$ in the adhesive composition can be found by measurement by the anion chromatography. If concretely described, the adhesive composition is diluted with pure water down to a concentration of 1%, and the obtained diluted solution is filtered through a syringe filter to remove the solid components. The concentration of the fluoride ions contained in the obtained filtrate is measured by the anion chromatography, and the amount of the fluoride ions in the dental adhesive composition is calculated.

<Other Components>

As described above, the dental adhesive composition of the present invention may be blended with monovalent metal ions, non-acidic polymerizable monomer (F), photopolymerization initiator (G) and various blending agents that have been known in per se. in the field of dentistry, in addition to being blended with the above-mentioned essential components (A) to (E).

Other Metal Ions (Monovalent Metal Ions):

The adhesive composition of the invention may contain monovalent metal ions as ion components other than the polyvalent metal ions (B) and the fluoride ions (E) so far as they do not seriously damage the effect of the invention. For instance, the total valence number of the monovalent metal ions contained in the adhesive composition is not more than 50% and, specifically, not more than 30% relative to the total valence number of the whole metal ions contained in the composition (sum of the total valence number of the polyvalent metal ions (B) and the total valence number of the monovalent metal ions). Namely, the total valence number ratio ($R_1$) of the monovalent metal ions to the whole metal ions is expressed by the following formula (4), $$R_1 = TV_1/TV_T \tag{4}$$

Wherein, $TV_1$ is a total valence number of the monovalent metal ions contained in the composition, and $TV_T$ is a total valence number of the whole metal ions contained in the composition, and is, desirably, in a range of not more than 0.5 and, specifically, not more than 0.3.

If the monovalent metal ions are present in large amounts, development of ionic bonds due to the polyvalent metal ions (B) is spoiled by the neutralization reaction of the monovalent metal ions with the acidic groups of the acidic group-containing polymerizable monomer (A), and the adhering strength may decrease.

Non-Acidic Polymerizable Monomers (F):

Further, the dental adhesive composition of the present invention may be blended with a polymerizable monomer without acidic group, i.e., may be blended with a non-acidic polymerizable monomer (F) as a polymerizable monomer component in addition to being blended with the above acidic group-containing polymerizable monomer (A). Any of a variety of non-acidic polymerizable monomers (F) may be selectively used depending on the object such as adjusting the strength on the interface of adhesion, permeability of the pretreating material into the tooth, and attaining more improved adhering strength to the tooth.

Any non-acidic polymerizable monomer (F) can be used without limitation. Specifically, the following various (meth) acrylate-type monomers can be used.

Mono(meth)acrylate-Type Monomers:
methyl(meth)acrylate,
ethyl(meth)acrylate,
glycidyl(meth)acrylate,
2-cyanomethyl(meth)acrylate,
benzyl(meth)acrylate,
polyethylene glycol mono(meth)acrylate,
allyl(meth)acrylate,
2-hydroxyethyl(meth)acrylate,
glycidyl(meth)acrylate,
3-hydroxypropyl(meth)acrylate,
glycerylmono(meth)acrylate, and
2-(meth)acryloxyethylacetylacetate.

Polyfunctional (meth)acrylate-Type Monomers:
ethylene glycol di(meth)acrylate,
diethylene glycol di(meth)acrylate,
triethylene glycol di(meth)acrylate,
nonaethylene glycol di(meth)acrylate,
propylene glycol di(meth)acrylate,
dipropylene glycol di(meth)acrylate,
2,2'-bis[4-(meth)acryloyloxyethoxyphenyl] propane,
2,2'-bis[4-(meth)acryloyloxyethoxyethoxyphenyl] propane,
2,2'-bis{4-[3-(meth)acryloyloxy-2-hydroxypropoxy]phenyl} propane,
1,4-butanediol di(meth)acrylate,
1,6-hexanediol di(meth)acrylate,
trimethylolpropane tri(meth)acrylate,
urethane (meth)acrylate, and
epoxy(meth)acrylate.

As the non-acidic polymerizable monomer (F), further, a polymerizable monomer other than the above (meth)acrylate-type monomer can be mixed and polymerized. As the other polymerizable monomers, there can be exemplified fumaric ester compounds such as dimethyl fumarate, diethyl fumarate and diphenyl fumarate; styrene compounds such as styrene, divinylbenzene, α-methylstyrene, and α-methylstyrene dimer; and allyl compounds such as diallyl phthalate, diallyl terephthalate, diallyl carbonate and allyl diglycol carbonate. The polymerizable monomers may be used alone or in a mixture of two or more kinds.

When a highly hydrophobic polymerizable monomer is used, further, it is desired to use an amphipatic monomer such as 2-hydroxyethyl (meth)acrylate or 2-hydroxypropyl (meth) acrylate to prevent separation of water and to maintain a homogeneous composition.

In the invention, from such a standpoint that the acidic group-containing polymerizable monomer (A) that is added exhibits its effect to a sufficient degree, it is desired that the non-acidic polymerizable monomer (F) is added in an amount of not more than 500 parts by mass and, more preferably, not more than 350 parts by mass per 100 parts by mass of the acidic group-containing polymerizable monomer (A).

Photopolymerization Initiators (G):

As described earlier, the adhesive composition of the present invention can be used as a pretreating material for tooth and as a dental adhesive. When used as the dental adhesive, however, it is necessary to add a photopolymerization initiator (G) to the adhesive composition to cure it.

As the photopolymerization initiator (G), there can be used a compound which by itself forms radical species upon being irradiated with light, or a mixture of this compound to which a polymerization promoter is added. Described below are examples of the compound which by itself undergoes the decomposition upon being irradiated with light and forms polymerizable radical species.

α-Diketones:
camphorquinone, benzyl, α-naphthyl, acetonaphthene, naphthoquinone, 1,4-phenanthrenequinone, 3,4-phenanthrenequinone, 9,10-phenanthrenequinone, etc.

Thioxanthones:
2,4-diethylthioxanthone, etc.

α-Aminoacetophenones:
2-benzyl-dimethylamino-1-(4-morpholinophenyl)-butanone-1,
2-benzyl-diethylamino-1-(4-morpholinophenyl)-butanone-1,
2-benzyl-dimethylamino-1-(4-morpholinophenyl)-propanone-1, 2-benzyl-diethylamino-1-(4-morpholinophenyl)-propanone-1,
2-benzyl-dimethylamino-1-(4-morpholinophenyl)-pentanone-1,
2-benzyl-diethylamino-1-(4-morpholinophenyl)-pentanone-1, etc.

Acylphosphinoxide Derivatives:
    2,4,6-trimethylbenzoyldiphenylphosphinoxide,
    bis(2,6-dimethoxybenzoyl)-2,4,4-trimethylpentylphosphinoxide, etc.

As the above polymerization initiator, there can be used tertiary amines, barbituric acids and mercapto compound. Described below are concrete examples thereof.

Tertiary Amines:
    N,N-dimethylaniline,
    N,N-diethylaniline,
    N,N-di-n-butylaniline,
    N,N-dibenzylaniline,
    N,N-dimethyl-p-toluidine,
    N,N-diethyl-p-toluidine,
    N,N-dimethyl-m-toluidine,
    p-bromo-N,N-dimethylaniline,
    m-chloro-N,N-dimethylaniline,
    p-dimethylaminobenzaldehyde,
    p-dimethylaminoacetophenone,
    p-dimethylaminobenzoic acid,
    ethyl p-dimethylaminobenzoate ester,
    amyl p-dimethylaminobenzoate ester,
    N,N-dimethylanthranic acid methyl ester,
    N,N-dihydroxyethylaniline,
    N,N-dihydroxyethyl-p-toludine,
    p-dimethylaminophenetyl alcohol,
    p-dimethylaminostilbene,
    N,N-dimethyl-3,5-xylidine,
    4-dimethylaminopyridine,
    N,N-dimethyl-α-naphthylamine,
    N,N-dimethyl-β-naphthylamine,
    tributylamine,
    tripropylamine,
    triethylamine,
    N-methyldiethanolamine,
    N-ethyldiethanolamine,
    N,N-dimethylhexylamine,
    N,N-dimethyldodecylamine,
    N,N-dimethylstearylamine,
    N,N-dimethylaminoethyl acrylate,
    N,N-dimethylaminoethyl methacrylate,
    2,2'-(n-butylimino)diethanol, etc.

Barbituric Acids:
    5-butylbarbituric acid,
    1-benzyl-5-phenylbarbituric acid, etc.

Mercapto Compounds:
    dodecyl mercaptane,
    pentaerythritoltetrakis(thioglycolate), etc.

There is no specific limitation on the amount of the photopolymerization initiator (G) if it is added in an amount effective for curing the adhesive composition, and the amount may be suitably selected. Generally, however, the photopolymerization initiator (G) is added in an amount in a range of 0.1 to 20 parts by mass and, specifically, 1 to 10 parts by mass per 100 parts by mass of the whole polymerizable monomers [(A)+(F)]. If the amount thereof is less than 0.1 parts by mass, the polymerization becomes insufficient. If the amount thereof exceeds 20 parts by mass, the strength of the formed polymer decreases, which is not desirable.

Other Blending Agents:

In the invention, there can be, further, added various blending agents that have been known per se. in the field of dentistry in addition to the above-mentioned components. As such blending agents, inorganic fillers (H) are representative examples. Acidic substances for adjusting pH have also been widely used.

The inorganic filler (H) is used to enhance the strength of the adhesive composition (e.g., pretreating material or adhesive) after cured and, specifically, to improve the durability of adhesion.

The inorganic filler (H) is different from the components (e.g., components (B'), (E'), (B'E') that will be described later) that are used as sources of polyvalent metal ions (B) and fluoride ions (E), since it does not elute out ions. Concrete examples of the inorganic filler (H) include composite inorganic oxides such as silica.zirconia, silica.titania, silica.alumina, as well as silica.

Though there is no specific limitation on the particle size of the inorganic filler (H), it is desired that the primary particle size is not larger than 5 μm, desirably, 0.001 to 1 μm and, more desirably, 0.01 to 0.5 μm. Further, there is no limitation on the shape of particles; i.e., the particles may be amorphous or spherical.

Upon being treated for its surfaces with a surface-treating agent as represented by the silane coupling agent, the inorganic filler (H) exhibits good affinity to the acidic group-containing polymerizable monomer (A) and exhibits further improved mechanical strength and water-resisting property.

As the silane coupling agent used for imparting hydrophobic property, the following compounds can be favorably used.
    methyltrimethoxysilane,
    methyltriethoxysilane,
    methyltrichlorosilane,
    dimethyldichlorosilane,
    trimethylchlorosilane,
    vinyltrimethoxysilane,
    vinyltriethoxysilane,
    vinyltrichlorosilane,
    vinyltriacetoxysilane,
    vinyltris(β-methoxyethoxy)silane,
    γ-methacryloyloxypropyltrimethoxysilane,
    γ-methacryloyloxypropyltris(β-methoxyethoxy)silane,
    γ-chloropropyltrimethoxysilane,
    γ-chloropropylmethyldimethoxysilane,
    γ-glycidoxypropyltrimethoxysilane,
    γ-glycidoxypropylmethyldiethoxysilane,
    β(3,4-epoxycyclohexyl)ethyltrimethoxysilane,
    N-phenyl-γ-aminopropyltrimethoxysilane, and
    hexamethyldisilazane, etc.

Though there is no specific limitation, the above inorganic filler (H) is, usually, added in an amount in a range of 10 to 200 parts by mass and, specifically, 20 to 100 parts by mass per 100 parts by mass of the acidic group-containing polymerizable monomer (A).

Further, the adhesive composition of the present invention exhibits acidic property since it is blended with the acidic group-containing polymerizable monomer (A) and, therefore, exhibits deliming action to the tooth and, hence, produces a large adhering strength even if no etching operation is conducted. To utilize the above advantages to a maximum degree, therefore, it is desired that the adhesive composition has a high acidity, e.g., has a pH of not higher than 4.8 and, preferably, in a range of 0.5 to 4.0 and, particularly preferably, 1.0 to 3.0.

Here, if the polyvalent metal ions (B) are present in a relatively large amount or if the monovalent metal ions are present in a large amount together with the polyvalent metal ions (B) relative to the acidic group-containing polymerizable monomer (A), then the adhesive composition may fail to exhibit a sufficient degree of acidity. In such a case, it is desired that the pH of the composition is adjusted to lie in the above range by using the acidic substance for adjusting the pH.

Here, the pH of the adhesive composition is a value measured at 25° C. by mixing the adhesive composition at a concentration of 10% by mass into ethanol and by using a pH meter that uses a pH electrode calibrated by using a neutral phosphate pH standard solution (pH 6.86) and a phthalate pH standard solution (pH 4.01). Ethanol used for the dilution should have a purity of not lower than 99.5%, and a pH value by ethanol alone of 4.8 to 5.0.

The present invention uses, as the acidic substance for adjusting the pH, an acidic compound having a group which is more weakly acidic than the acidic group possessed by the acidic group-containing polymerizable monomer (A) and, specifically, more weakly acidic than the hydrogenphosphoric diester group.

For instance, the hydrogenphosphoric diester group has a pKa-value of 2.15 in water of 25° C., and there is used a weakly acidic compound having a pKa-value in excess thereof. This is because if there is used a substance more strongly acidic than the hydrogenphosphoric diester group, then no ionic bond is formed between the polyvalent metal ions (B) and the hydrogenphosphoric diester groups of the phosphoric diester monomer (A-1).

From the standpoint of maintaining the function for preventing precipitation without impairing the ionic bond between the fluoride ions F⁻ and the polyvalent metal ions (B), it is further, desired that the acidic substance that is used for adjusting the pH is a weakly acidic compound having a pKa-value which is larger than the above pKa-value of 3.17 of the hydrofluoric acid.

From the standpoint of a strong deliming function to the tooth, furthermore, it is desired that the acidic substance for adjusting the pH has a pKa-value which is not larger than 6.0 and, particularly, not larger than 4.0.

Suitable examples of the acidic substance for adjusting the pH include citric acid, tartaric acid, malonic acid, glycolic acid, lactic acid, phthalic acid, isophthalic acid, terephthalic acid and methoxyacetic acid.

As described above, the acidic substance for adjusting the pH is a substance more weakly acidic than the hydrogenphosphoric diester group. Still more, from the size of their ionic radius, the ions of the weakly acidic substance, usually, ionically bond to the polyvalent metal ions (B) considerably weakly as compared to the fluoride ions (E).

If added in too large amounts in an attempt to adjust the pH, however, the acidic substance for adjusting the pH may hinder the polyvalent metal ions (B) from smoothly and ionically bonding to the acidic groups of the acidic group-containing polymerizable monomer (A), specifically, to the hydrogenphosphoric diester groups of the phosphoric diester monomer (A-1) and, further, to the fluoride ions (E). Therefore, in case the pH is to be adjusted by using the above acidic compound, it is desired that the content of the acidic substance for adjusting the pH is not more than 15% by mole and, specifically, not more than 10% by mole per the whole acidic compounds (acidic group-containing polymerizable monomer (A)+fluoride ions (E)+acidic substance for adjusting the pH).

As the blending agents other than the inorganic filler (H) and the acidic substance for adjusting the pH, there can be, further, suitably added an organic viscosity-increasing agent such as polyvinyl pyrrolidone, carboxymethyl cellulose or polyvinyl alcohol, as well as ultraviolet-ray absorber, dye, antistatic agent, pigment and perfume in ranges in which they do not lower the performance of the adhesive composition.

<Production of the Dental Adhesive Compositions>

The dental adhesive composition of the present invention is produced by mixing the above-mentioned acidic group-containing polymerizable monomer (A), polyvalent metal ions (B), water (C), water-soluble organic solvent (D), fluoride ions (E) and various components that are to be suitably blended together at predetermined ratios, and ripening the mixture so that the above-mentioned valence number ratio ($R_F$) lies within a predetermined range. In this case, a polyvalent metal ion-releasing component (B') is used as a source of polyvalent metal ions (B) and a fluoride ion-releasing component (E') is used as a source of fluoride ions (E). It is, however, also allowable to use, as the components (B') and (E'), a multi-ion-releasing component (B'E') that releases polyvalent metal ions and fluoride ions.

(1) Polyvalent Metal Ion-Releasing Components (B'):

The polyvalent metal ion-releasing component (B') can be used without limitation if it is capable of releasing the above-mentioned polyvalent metal ions (B) in such an amount that the valence ratio ($R_F$) lies within the predetermined range when the adhesive composition is prepared by being mixed together with other components.

Concretely, there can be used a polyvalent simple metal, a polyvalent metal compound and a polyvalent metal ion-eluting filler. The polyvalent simple metal is very little soluble in water and requires a very long period of time (i.e., requires a very long period of time for ripening) until it is dissolved in a sufficient amount in the above-mentioned acidic group-containing polymerizable monomer (A). In the invention, therefore, the polyvalent metal compound and the polyvalent metal ion-eluting filler are preferred.

(1-1) Polyvalent Metal Compounds:

As the polyvalent metal compound, there can be used an acid having a pKa-value at least higher than the pKa-value which is based on the first dissociation of the hydrogenphosphoric diester group, i.e., there can be used a metal salt which is more weakly acidic than the hydrogenphosphoric diester group. This is because if a salt which is more strongly acidic than the hydrogenphosphoric diester group is used, the ionic bond does not develop to a sufficient degree between the free polyvalent metal ions and the hydrogenphosphoric diester groups of the polymerizable hydrogenphosphoric diester monomer.

As the polyvalent metal salt more weakly acidic than the hydrogenphosphoric diester group, there can be exemplified carbonate, enolate of 1,3-diketone, citrate, tartarate, malonate, glycolate, lactate, phthalate, isophthalate, terephthalate, acetate and metoxyacetate.

As will be described later, some of these weakly acidic polyvalent metal salts are very little soluble in water. It is, therefore, recommended to confirm their solubilities by conducting experiments in advance and use them upon making sure if the polyvalent metal ions (B) can be released in amounts to satisfy the predetermined total valence number ratio ($R_P$).

Further, the polyvalent metal compound can also be used in the form of a hydroxide, a hydride or an alkoxide.

Among the above polyvalent metal compounds according to the invention, it is desired to use a hydroxide, a hydride, a carbonate or a lower alkoxide having not more than 4 carbon atoms since they permit polyvalent metal ions (B) to be quickly eluted out (ripening time is short), form by-products that are gases at normal temperature, or form water or lower alcohols which can be easily removed when the composition is applied to the tooth surfaces, and do not adversely affect the adhering strength. The hydroxide, alkoxide and carbonate are further preferred from the standpoint of easy handling.

Described below are concrete polyvalent metal compounds that can be particularly preferably used in the invention as the polyvalent metal ion-releasing component (B').
  aluminum methoxide,
  aluminum isopropoxide,
  aluminum hydroxide,
  aluminum acetylacetonato,
  gallium ethoxide,
  indium ethoxide
  scandium isopropoxide,
  yttrium isopropoxide,
  lanthanum methoxide,
  lanthanum ethoxide,
  lanthanum isopropoxide,
  lanthanum hydroxide,
  lanthanum carbonate,
  cerium isopropoxide,
  praseodymium isproxide,
  promethium isopropoxide,
  neodymium isopropoxide,
  samarium isopropoxide,
  europium acetylacetonato,
  gadolinium acetylacetonato,
  terbium acetylacetonato,
  dysprosium acetylacetonato,
  holmium acetylacetonato,
  erbium acetylacetonato,
  thulium acetylacetonato,
  ytterbium isopropoxide,
  ytterbium acetylacetonato,
  lutetium acetylacetonato, etc.

In the invention, the following polyvalent metal compounds are most desired among the above-exemplified compounds.
  aluminum methoxide,
  aluminum isopropoxide,
  aluminum hydroxide,
  lanthanum methoxide,
  lanthanum ethoxide,
  lanthanum isopropoxide,
  lanthanum hydroxide,
  lanthanum carbonate, etc.

Many of the oxides and carboxylates of aluminum and lanthanum are insoluble in the polymerizable monomer or organic solvent and, generally, require very extended periods of time for the polyvalent metal ions (B) to be eluted out in the above required amount even in the presence of water, and are not, therefore, suited for use as the polyvalent metal ion-releasing component (B') which is the source of polyvalent metal ions. Specifically, the oxides of aluminum and lanthanum do not almost elute out their metal ions even in the presence of water, and cannot, usually, be used as the polyvalent metal ion-releasing component (B').

(1-2) Polyvalent Metal Ion-Eluting Fillers:

The polyvalent metal ion-eluting filler used as a source of polyvalent metal ions (B) is capable of eluting out the polyvalent metal ions (B) in the dental adhesive composition which is acidic but does not substantially elute out conjugated base ions of a strong acid having a pKa-value smaller than the pKa-value which is based on the first dissociation of the hydrogenphosphoric diester group.

As the above filler, usually, there can be used glasses (e.g., oxide glasses) having skeletons of a chain-like, lamellar or mesh-like structure holding polyvalent metal ions (B) in the gaps of the skeletons. Oxide glasses are, for example, aluminosilicate glass, borosilicate glass and the like glasses. There can be, further, used a soda lime glass containing polyvalent metal ions.

The above polyvalent metal ion-eluting filler has no specific limitation on the shape thereof, and may comprise amorphous particles or spherical particles as obtained by pulverization or may, as required, be mixed with plate-like or fibrous particles. From the standpoint of easily producing the homogeneous adhesive composition, the average particle size ($D_{50}$) calculated as the volume is in a range of 0.01 μm to 5 μm, specifically, 0.05 μm to 3 μm and, most desirably, 0.1 μm to 2 μm as measured by the laser diffraction/light scattering method.

From the standpoint of easily adjusting the valence number ratio ($R_F$) to lie in the above-mentioned range, further, it is desired that the polyvalent metal ion-eluting filler is such that when 0.1 g of the filler is dipped and held in 10 ml of an aqueous solution containing 10% by weight of a maleic acid at a temperature of 23° C. for 24 hours, the polyvalent metal ions are eluted out in an amount of 5.0 to 500 meq/g of filler and, specifically, 10 to 100 meq/g of filler.

Here, the eluted amount (meq) of the polyvalent metal ions corresponds to the amount (milliequivalent) of the polyvalent metal ions (B) that can be ionically bonded to a gram of the acidic group-containing polymerizable monomer (A).

Further, the total valence number of the polyvalent metal ions (B) per gram of the acidic group-containing polymerizable monomer (A) eluted out from the polyvalent metal ion-eluting filler is the sum of values obtained by multiplying the amounts (mmols/g) of the respective kinds of the polyvalent metal ions (B) per gram of the acidic group-containing polymerizable monomer (A) by the valence numbers of the respective kinds of the polyvalent metal ions.

Further, the concentrations of the respective kinds of the polyvalent metal ions can be measured by the ICP emission spectroscopy or the atomic absorption spectroscopy.

The polyvalent metal ions (B) are, usually, eluted out from the polyvalent metal ion-eluting filler almost completely if left to stand at room temperature (23° C.) for 3 hours to 12 hours after the polyvalent metal ion-eluting filler has been added to the acidic group-containing polymerizable monomer (A). If the amount of elution is larger than the amount required by the invention, it is desired to control the eluting characteristic by pretreating the polyvalent metal ion-eluting filler by a widely known method. Namely, as a representative method, the polyvalent metal ion-eluting filler is suitably pretreated with an acid to, first, remove the polyvalent metal ions (B) from the surface portions of the filler to thereby lower the total amount of elution.

In the invention, further, when the polyvalent metal ion-eluting filler is the multi-ion-releasing component (B'E') that also serves as a source of fluoride ions (E), such as fluoroaluminosilicate glass as will be described later, the elution of the fluoride ions (E) decreases much more than the elution of the above polyvalent metal ions (B). Therefore, if the polyvalent metal ion-eluting filler is simply added to the acidic group-containing polymerizable monomer (A), the fluoride ions (E) tend to become insufficient contrary to the case of the above polyvalent metal ions (B) even if the fluoride ions were contained in sufficient amounts in the particles thereof. It is, therefore, desired to control the elution characteristic of the fluoride ions (E), too, by conducting the same operation as that of pretreating the above polyvalent metal ion-eluting filler with the acid. That is, upon suitably pretreating the polyvalent metal ion-eluting filler with the acid, easiness can be greatly improved for eluting the fluoride ions.

The acid used for this method is a widely known acid such as inorganic acid like hydrochloric acid or nitric acid, or organic acid such as maleic acid or citric acid. The concentration of acid and the treating time may be suitably determined depending upon the amount of the polyvalent metal ions to be removed and the eluting characteristic of the fluoride ions to be improved. Here, attention should be given to that if the treatment with the acid is conducted to an excess, then the polyvalent metal ions (B) and often the fluoride ions (E) may be excessively removed, and the value specified by the invention may not be satisfied.

After the polyvalent metal ions (B) have been eluted out, the polyvalent metal ion-eluting filler comprising the above-mentioned glasses, usually, assumes the form of porous particles which, if left to remain in the composition, work as a reinforcing material contributing to improving the strength of the cured body. However, these porous particles may aggregate or may have large particle sizes, and often precipitate in the composition. Depending on the cases, therefore, it is desired to remove such particles by filtration or the like.

(2) Fluoride Ion-Releasing Components (E'):

When mixed together with the other components to prepare the adhesive composition, the fluoride ion-releasing component (E') which is the source of fluoride ions (E) works to release fluoride ions F⁻ in such an amount that the valence number ratio ($R_F$) can be set to lie in the predetermined range, and may be a hydrofluoric acid, an alkali metal fluoride or ammonium fluorides.

Specifically preferred fluoride ion-releasing component (E') is an alkali metal fluoride and, concretely, a sodium fluoride, potassium fluoride, lithium fluoride or the like.

When the alkali metal fluoride is used as the fluoride ion-releasing component (E'), alkali metal ions which are monovalent metal ions are released into the composition in addition to the fluoride ions. As described above, it is desired that the amount of the fluoride ion-releasing component (E') that is added is so adjusted that the ratio of the total ionic valence number of the monovalent metal ions is not more than 0.5 and, specifically, not more than 0.3 relative to the total valence number of the whole metal ions contained in the composition (sum of the total valence number of the polyvalent metal ions and the total valence number of the monovalent metal ions).

(3) Multi-Ion-Releasing Components (B'E'):

In the invention, the polyvalent metal ions (B) and the fluoride ions (E) may be fed from a common source of release. Namely, a multi-ion-releasing component (B'E') capable of releasing the polyvalent metal ions and the fluoride ions can be used in place of the above-mentioned polyvalent metal ion-releasing component (B') and the fluoride ion-releasing component (E'), or can be used together with these components.

As the component (B'E'), there can be exemplified fluoride glasses such as fluoroaluminosilicate glass and zirconium fluoride glass; alkaline earth metal fluorides such as calcium fluoride and magnesium fluoride; earth metal fluorides such as aluminum fluoride, yttrium fluoride, lanthanum fluoride and ytterbium fluoride; zinc fluoride, and the like.

As the fluoride glass, it is desired to use the fluoroaluminosilicate glass. The fluoroaluminosilicate glass may be the known one that has been used for the dental cement such as glass ionomer cement. The fluoroaluminosilicate glass contains aluminum ions in large amounts as polyvalent metal ions and may often, further, contain other polyvalent metal ions such as of lanthanum.

Described below is the composition of a representative fluoroaluminosilicate glass.

silicon: 10 to 33% by mass
aluminum: 4 to 30% by mass
alkaline earth metal: 5 to 36% by mass
alkali metal: 0 to 10% by mass
phosphorus: 0.2 to 16% by mass
fluorine: 2 to 40% by mass
oxygen: remainder Described below is the composition of the fluoroaluminosilicate glass that is most favorably used in the present invention.

silicon: 15 to 25% by mass
aluminum and lanthanum: 10 to 40% by mass
alkaline earth metal: 5 to 10% by mass
alkali metal: 0 to 1% by mass
phosphorus: 0.5 to 5% by mass
fluorine: 4 to 40% by mass
oxygen: remainder As required, there can be further preferably used a composition in which aluminum is partly substituted by other earth metals such as scandium, yttrium and ytterbium.

As for the amounts of elution of the polyvalent metal ions and fluoride ions F⁻ from the fluoride glass, the fluoride ions elute out less than the polyvalent metal ions as described above. Therefore, after the components are mixed together like the above polyvalent metal ion-eluting filler, the mixture is ripened at room temperature (23° C.) for not less than 10 hours and, preferably, not less than 12 hours so that the amount is stabilized maintaining a predetermined relationship. As described above, further, there is used the fluoride glass that has been adjusted by the pretreatment with the acid so that the fluoride ions can be easily eluted out. The ripening time can be shortened upon suitably conducting the heating. In case the valence number ratio ($R_F$) calculated from the eluted amounts of the polyvalent metal ions and fluoride ions fails to lie in the predetermined range (0.2 to 2.0), the above-mentioned polyvalent metal ion-releasing component (B') and the fluoride ion-releasing component (E') may be suitably so mixed together that the valence number ratio ($R_F$) lies in the predetermined range.

It is, further, desired that the fluoride glass is used in the form of a powder having an average particle size ($D_{50}$) the same as that of the above-mentioned polyvalent metal ion-eluting filler.

(4) Mixing and Ripening the Components:

The dental adhesive composition of the invention is obtained by homogeneously mixing the above polyvalent metal ion-releasing component (B') and the fluoride ion-releasing component (E') (and/or the multi-ion-releasing component (B' E') together with the other fundamental components (A), (C) and (D), as well as the other components that are suitably used, at the above-mentioned ratios, and ripening them.

In mixing the components, the amounts of the polyvalent metal ion-releasing component (B'), the fluoride ion-releasing component (E') or the multi-ion-releasing component (B' E') used as the source of polyvalent metal ions (B) and fluoride ions (E), are so selected that the valence number ratio ($R_F$) lies in the predetermined range and, more preferably, that the total valence number ratio ($R_P$), too, lies in the predetermined range depending upon the amounts of the polyvalent metal ions and fluoride ions released due to the ripening conducted for a predetermined period of time and upon the amounts of the other components that are added.

The components may be mixed together according to a known method that has been employed for the dental pretreating materials and dental adhesives. Usually, the components to be added are weighed under inert light such as red light, and are stirred together until a homogeneous solution is obtained.

After the components have been mixed together, the mixture is ripened, i.e., held under suitably heated or stirring conditions depending upon the kinds and compositions of the sources (components (B'), (E'), (B' E')) of the polyvalent metal ions (B) and fluoride ions (E) for a period of time until at least the ions that can be released are all released. When the fillers or glasses are used, the ripening time is not shorter than 10 hours and, preferably, not shorter than 12 hours at room temperature (23° C.). By heating up to about 30 to 40° C., however, the ripening time can be shortened. When metal salts are used as the sources, further, the ripening time is about several minutes at room temperature. When alkoxides are used, too, the ripening time is about several minutes at room temperature. In either case, a suitable ripening time may be determined by conducting experiments in advance.

The dental adhesive composition thus prepared of the present invention assumes the state of one solution, i.e., one package. At the time of use, therefore, no cumbersome operation is necessary, such as mixing the components together, enabling dentists to save their labor and, further, assuring a stable and predetermined adhering strength.

<Use of the Dental Adhesive Composition>

When blended with the photopolymerization initiator (G), the thus obtained adhesive composition of the invention by itself can be used as a dental adhesive, e.g., as an adhesive for composite resins, as an adhesive for brackets or as an adhesive for prosthetic materials.

When no photopolymerization initiator (G) is blended, the adhesive composition is used as a tooth pretreating agent. The pretreating agent has the functions of both etching the tooth and promoting the permeation into the tooth, and can be used as a self-etching primer for adhering the composite resin, bracket or prosthetic material to the tooth. Namely, the pretreating agent may be applied onto the tooth prior to applying the adhesive that is used for adhering the prosthetic material or the like to the tooth.

The above dental adhesive may be of the type of chemical polymerization. For the use of adhering the composite resin or the bracket, however, it is desired that the dental adhesive is of the photocuring type from the standpoint of easy handling. As the photocurable dental adhesive, there can be used any known adhesive without limitation. For adhering the composite resins, for example, there can be used those that have been described in JP-A-6-9327, JP-A-6-24928 and JP-A-8-319209. For adhering the brackets, there can be used those described in JP-T-2005-529637, JP-T-2004-510796 and JP-A-5-85912.

EXAMPLES

The invention will now be concretely described by way of Examples and Comparative Examples to which only, however, the invention is in no way limited. Abbreviated words and symbols appearing in Examples are as described below.
Acidic Group-Containing Polymerizable Monomers (A) (Hereinafter "Acidic Monomers").
Hydrogenphosphoric Diester Monomers (A-1).
  PM2: bis(2-methacryloyloxyethyl)hydrogenphosphate
  6PPH: 6-methacryloyloxyhexylphenyl hydrogenphosphate
Other Acidic Group-Containing Polymerizable Monomers (A-2).
  PM1: 2-methacryloyloxyethyl dihydrogenphosphate
  MAC-10: 11-methacryloyloxyundecane-1,1-dicarboxylic acid Non-Acidic Polymerizable Monomers (F) (Hereinafter "Non-Acidic Monomers").
  BisGMA: 2,2'-bis[4-(2-hydroxy-3-methacryloyloxy propoxy)phenyl] propane
  3G: triethylene glycol dimethacrylate
  HEMA: 2-hydroxyethyl methacrylate
Polyvalent Metal Ion-Releasing Components (B').
  Al(O-i-Pr)$_3$: aluminum triisopropoxide
  La(O-i-Pr)$_3$: lanthanum triisopropoxide
Fluoride Ion-Releasing Component (E').
  FNa: sodium fluoride
Multi-Ion-Releasing Components (B'E').
  MF1: ion-eluting filler obtained by milling a fluoroaluminosilicate glass powder (Tokuso Ionomer, manufactured by Tokuyama Dental Co.) into an average particle size of 0.5 μm by using a wet-type continuous ball mill (New My-Mill, manufactured by Mitsui Kozan Co.), and treating the filler surfaces with 20 g of 5.0-N hydrochloric acid per gram of the powder for 15 minutes.
    Average particle size: 0.5 μm
    Amount of ions eluted out in 24 hours: 27 meq/g of filler
  MF2: ion-eluting filler obtained by milling a fluoroaluminosilicate glass powder (Tokuso Ionomer, manufactured by Tokuyama Dental Co.) into an average particle size of 0.5 μm by using a wet-type continuous ball mill (New My-Mill, manufactured by Mitsui Kozan Co.), and treating the filler surfaces with 20 g of 5.0-N hydrochloric acid per gram of the powder for 40 minutes.
    Average particle size: 0.5 μm
    Amount of ions eluted out in 24 hours: 10 meq/g of filler
  MF3: ion-eluting filler obtained by milling a fluoroaluminosilicate glass powder (Tokuso Ionomer, manufactured by Tokuyama Dental Co.) into an average particle size of 0.5 μm by using a wet-type continuous ball mill (New My-Mill, manufactured by Mitsui Kozan Co.).
    Average particle size: 0.5 μm
    Amount of ions eluted out in 24 hours: 50 meq/g of filler
Water-Soluble Organic Solvent (D).
  IPA: isopropyl alcohol
Photopolymerization Initiator (G).
  CQ: camphor quinone
  DMBE: ethyl p-N,N-dimethylaminobenzoate
Inorganic Fillers (H).
  F1: amorphous silica of a particle size of 0.02 μm (treated with a methylchlorosilane)
  F2: a mixture of spherical silica-zirconia of a particle size of 0.4 μm (treated with a γ-methacryloyloxypropyltrimethoxysilane to be hydrophobic) and spherical silica-titania of a particle size of 0.08 μm (treated with a γ-methacryloyloxypropyltrimethoxysilane to be hydrophobic) at a mass ratio of 70:30.

In the following Examples and Comparative Examples, measurements were taken according to the following methods.

(1) Measurement of Polyvalent Metal Ions:

The adhesive composition of the invention was prepared, and stirred for 24 hours. 0.2 Grams of the composition was taken into a 100-ml sample tube and was diluted with IPA to 0.1% by mass. The solution was filtered through a syringe filter, and the filtrate was measured for the concentrations of metal ions (mmols/g) contained in 100 parts by mass of the polymerizable monomer relying upon the ICP (induction-coupled plasma) emission spectroscopic analysis. The concentrations of the respective kinds of the metal ions were calculated by using calibration curves found from the standard samples (1 ppm, 2.5 ppm, 6 ppm) of the respective kinds of ions.

(2) Measurement of Fluorine Ions:

2 Grams of the adhesive composition, 100 g of water and 10 g of diethyl ether were vigorously mixed together, left to stand still, the aqueous phase thereof was filtered through the syringe filter, and the obtained filtrate was measured by using an ion chromatography to measure the concentration of fluorine ions (mmols/g) contained in 100 parts by mass of the polymerizable monomer. The concentration of the fluorine ions was calculated by using a calibration curve found from the standard samples of fluorine ions (10 ppm, 25 ppm, 50 ppm).

(3) Evaluating the Adhesion to the Tooth.

(a) Preparation of an Adhesion Test Piece:

Within 24 hours after the slaughter, a bovine foretooth was pulled out, and the enamel surface and the dentin surface were ground by using a #600 emery paper while pouring water so as to be in parallel with the labial face to thereby prepare a tooth for testing the strength.

Next, the compressed air was blown onto the above surface of the tooth for testing the strength for about 10 seconds to dry the surface and, thereafter, a double-sided adhesive tape having a hole of 3 mm in diameter perforated therein was fixed to either the enamel surface or the dentin surface. Next, a paraffin wax of a thickness of 0.5 mm having a hole of 8 mm in diameter perforated therein was fixed onto the above hole in concentric therewith to form a mimic cavity.

A sample adhesive composition was applied into the mimic cavity, left to stand for 20 seconds and, thereafter, the compressed air was blown thereto for about 10 seconds to dry the composition followed by the irradiation with light from a dental visible ray irradiator (Tokuso Powerlight, manufactured by Tokuyama Co.) for 10 seconds. Further, a dental composite resin (Estelite Σ, manufactured by Tokuyama Dental Co.) was applied thereon, and was irradiated with light from the visible ray irradiator for 30 seconds to prepare an adhesion test piece.

(b) Method of Testing the Adhesion.

The above adhesion test piece was dipped in water of 37° C. for 24 hours and was, thereafter, pulled by using a tension tester (Autograph manufactured by Shimazu Seisakusho Co.) at a crosshead speed of 2 mm/min. to measure the tensile adhering strength between the dentin and the composite resin. Four test pieces were measured for their adhering strength per a test relying upon the above method, and an average value thereof was regarded as an adhering strength to the enamel or to the dentin to evaluate the adhesion to the tooth.

(4) Testing the Storage Stability.

(a) Evaluating the Salt Precipitation.

After the adhesive composition was prepared, 10 g of the adhesive composition was introduced into a 20-ml glass bottle and was stored in an incubator maintained at 37° C. Precipitation of a white solid matter from the adhesive composition was observed by the eye with the passage of time, and the timings of the salt precipitation were evaluated on the basis of the following three steps.

⊚: No salt precipitation was observed even after two months have passed.
○: Slightly precipitated (precipitated on the bottom of the glass bottle). Number of days until precipitated was recorded.
X: White solid matter precipitated in large amounts within 3 days (the liquid was cloudy).

(b) Evaluating the Gelling Property.

10 Grams of the sample adhesive composition was introduced into the 20-ml glass bottle and was stored in the incubator maintained at 37° C. Gellation of the adhesive composition was observed by the eye with the passage of time, and the gellation timings were evaluated on the basis of the following three steps.

⊚: The solution was not gelled even after two months have passed.
○: The solution was not gelled for more than one month. The number of days until gelled was recorded.
X: The liquid gelled within 3 days.

Example 1

The components were weight out according to the following recipe, and were stirred and mixed together at room temperature (23° C.) for 24 hours to prepare a dental adhesive.

Grams of PM2/hydrogenphosphoric diester monomer (A-1),
2 Grams of Al(O-1-pr)$_3$/polyvalent metal ion source (B'),
0.4 Gram of FNa/fluoride ion source (E'),
34 Grams of IPA/water-soluble organic solvent (D),
7.6 Grams of water, and
0.4 Grams of CQ and 0.4 g of DMBE/photopolymerization initiator (G).

The adhesive was measured for its amount of polyvalent metal ions and amount of fluorine ions. Thereafter, the adhesive was tested for its adhesion and was evaluated for its adhesion to the enamel and to the dentin. The adhesive was, further, tested for its storage stability and was evaluated for its salt precipitation and gelling property. The composition of the adhesive was as shown in Table 1 and the measured results were as shown in Tables 2 and 3.

Examples 2 to 22

Dental adhesives of compositions shown in Table 1 were prepared according to the method of Example 1.

The obtained adhesives were measured for their amounts of polyvalent metal ions and amounts of fluorine ions, and were tested for their adhesion and storage stability in the same manner as in Example 1 to obtain results as shown in Tables 2 and 3.

Comparative Examples 1 to 12

Adhesives of compositions shown in Table 4 were prepared according to the method of Example 1.

The obtained adhesives were measured for their amounts of polyvalent metal ions and amounts of fluorine ions, and were tested for their adhesion and storage stability in the same manner as in Example 1 to obtain results as shown in Tables 5 and 6.

TABLE 1

| | Acidic monomer (A) | | | | | | |
|---|---|---|---|---|---|---|---|
| | (A-1) | | (A-2) | | | | (C) |
| | PM2 | 6PPH | PM1 | MAC-10 | (B')* | (E')* | Water |
| Ex. 1 | 100 | | | | Al(O-i-pr)3 (20) | FNa(4) | 76 |
| Ex. 2 | | 100 | | | Al(O-i-pr)3 (20) | FNa(4) | 76 |
| Ex. 3 | 60 | | 40 | | Al(O-i-pr)3 (20) | FNa(4) | 76 |
| Ex. 4 | 60 | | 40 | | Al(O-i-pr)3 (6) | FNa(1.2) | 76 |

TABLE 1-continued

| | | | | | | |
|---|---|---|---|---|---|---|
| Ex. 5 | 100 | | | Al(O-i-pr)3 (63) | FNa(13) | 76 |
| Ex. 6 | 60 | | 40 | Al(O-i-pr)3 (20) | FNa(2.8) | 76 |
| Ex. 7 | 60 | | 40 | Al(O-i-pr)3 (20) | FNa(23) | 76 |
| Ex. 8 | 60 | | 40 | Al(O-i-pr)3 (20) | FNa(4) | 76 |
| Ex. 9 | 60 | | 40 | Al(O-i-pr)3 (20) | FNa(4) | 76 |
| Ex. 10 | 60 | | 40 | La(O-i-pr)3 (32) | FNa(4) | 76 |
| Ex. 11 | 60 | | 40 | Al(O-i-pr)3 (16) La(O-i-pr)3 (8) | FNa(4) | 76 |
| Ex. 12 | | 60 | 40 | Al(O-i-pr)3 (16) La(O-i-pr)3 (8) | FNa(4) | 76 |
| Ex. 13 | 60 | | 40 | MF1 (24) | (B'E') | 76 |
| Ex. 14 | 60 | | 40 | MF1 (40) | (B'E') | 76 |
| Ex. 15 | 60 | | 40 | MF1 (24) | (B'E') | 76 |
| Ex. 16 | 60 | | 40 | MF1 (24) | (B'E') | 76 |

| | (D) Solvent | (F) Non-acidic monomer | | | (G) Initiator | (H) Filler |
|---|---|---|---|---|---|---|
| | | BisGMA | 3G | HEMA | | |
| Ex. 1 | IPA(340) | | | | CQ(4.0), DMBE(4.0) | |
| Ex. 2 | IPA(340) | | | | CQ(4.0), DMBE(4.0) | |
| Ex. 3 | IPA(340) | | | | CQ(4.0), DMBE(4.0) | |
| Ex. 4 | IPA(340) | | | | CQ(4.0), DMBE(4.0) | |
| Ex. 5 | IPA(340) | | | | CQ(4.0), DMBE(4.0) | |
| Ex. 6 | IPA(340) | | | | CQ(4.0), DMBE(4.0) | |
| Ex. 7 | IPA(340) | | | | CQ(4.0), DMBE(4.0) | |
| Ex. 8 | IPA(340) | 120 | 80 | | CQ(4.0), DMBE(4.0) | |
| Ex. 9 | IPA(340) | 120 | 80 | 100 | CQ(4.0), DMBE(4.0) | |
| Ex. 10 | IPA(340) | 120 | 80 | 100 | CQ(4.0), DMBE(4.0) | |
| Ex. 11 | IPA(340) | 120 | 80 | 100 | CQ(4.0), DMBE(4.0) | |
| Ex. 12 | IPA(340) | 120 | 80 | 100 | CQ(4.0), DMBE(4.0) | |
| Ex. 13 | IPA(340) | 120 | 80 | 100 | CQ(4.0), DMBE(4.0) | |
| Ex. 14 | IPA(340) | 120 | 80 | 100 | CQ(4.0), DMBE(4.0) | |
| Ex. 15 | IPA(340) | 120 | 80 | 100 | CQ(4.0), DMBE(4.0) | F1(40) |
| Ex. 16 | IPA(340) | 120 | 80 | 100 | CQ(4.0), DMBE(4.0) | F2(40) |

| | Acidic monomer (A) | | | | (B')* | (E')* | (C) Water |
|---|---|---|---|---|---|---|---|
| | (A-1) | | (A-2) | | | | |
| | PM2 | 6PPH | PM1 | MAC-10 | | | |
| Ex. 17 | | | 60 | 40 | Al(O-i-pr)3 (16) La(O-i-pr)3 (8) | FNa(4) | 15 |
| Ex. 18 | | | 60 | 40 | Al(O-i-pr)3 (16) La(O-i-pr)3 (8) | FNa(4) | 110 |
| Ex. 19 | | | 60 | 40 | Al(O-i-pr)3 (16) La(O-i-pr)3 (8) | FNa(4) | 76 |
| Ex. 20 | | | 60 | 40 | Al(O-i-pr)3 (16) La(O-i-pr)3 (8) | FNa(4) | 76 |
| Ex. 21 | | | 60 | 40 | Al(O-i-pr)3 (16) La(O-i-pr)3 (8) | FNa(4) | 76 |
| Ex. 22 | | | 48 | 52 | Al(O-i-pr)3 (16) La(O-i-pr)3 (8) | FNa(4) | 76 |

| | (D) Solvent | (F) Non-acidic monomer | | | (G) Initiator | (H) Filler |
|---|---|---|---|---|---|---|
| | | BisGMA | 3G | HEMA | | |
| Ex. 17 | IPA(340) | 120 | 80 | 100 | CQ(4.0), DMBE(4.0) | |
| Ex. 18 | IPA(340) | 120 | 80 | 100 | CQ(4.0), DMBE(4.0) | |
| Ex. 19 | IPA(120) | 120 | 80 | 100 | CQ(4.0), DMBE(4.0) | |
| Ex. 20 | IPA(580) | 120 | 80 | 100 | CQ(4.0), DMBE(4.0) | |
| Ex. 21 | IPA(340) | 160 | 120 | 180 | CQ(4.0), DMBE(4.0) | |
| Ex. 22 | IPA(340) | 120 | 80 | 100 | CQ(4.0), DMBE(4.0) | |

*(B'): Polyvalent metal ion-releasing component, (E'): Fluoride ion-releasing component, (B'E'): Multi-ion-releasing component.

TABLE 2

| | (*1) | $TV_A$ | Amount of polyvalent metal ions/mmols | (*2) | $TV_P$ | $R_F$ ($V_F/TV_P$) | $R_P$ ($TV_P/TV_A$) |
|---|---|---|---|---|---|---|---|
| Ex. 1 | 100 mole % | 0.62 | $Al^{3+}$ (96.6) | 95.2 | 0.29 | 0.33 | 0.47 |
| Ex. 2 | 100 mole % | 0.61 | $Al^{3+}$ (96.6) | 95.2 | 0.29 | 0.33 | 0.47 |
| Ex. 3 | 49.5 mole % | 0.56 | $Al^{3+}$ (96.6) | 95.2 | 0.29 | 0.33 | 0.51 |

TABLE 2-continued

| | (*1) | $TV_A$ | Amount of polyvalent metal ions/mmols | (*2) | $TV_P$ | $R_F$ ($V_F/TV_P$) | $R_P$ ($TV_P/TV_A$) |
|---|---|---|---|---|---|---|---|
| Ex. 4 | 49.5 mole % | 0.56 | $Al^{3+}$ (29) | 29.0 | 0.090 | 0.33 | 0.15 |
| Ex. 5 | 100 mole % | 0.62 | $Al^{3+}$ (304) | 310.0 | 0.91 | 0.34 | 1.47 |
| Ex. 6 | 49.5 mole % | 0.56 | $Al^{3+}$ (96.6) | 66.8 | 0.29 | 0.23 | 0.51 |
| Ex. 7 | 49.5 mole % | 0.56 | $Al^{3+}$ (96.6) | 548.0 | 0.29 | 1.9 | 0.51 |
| Ex. 8 | 49.5 mole % | 0.56 | $Al^{3+}$ (96.6) | 95.2 | 0.29 | 0.33 | 0.51 |
| Ex. 9 | 49.5 mole % | 0.56 | $Al^{3+}$ (96.6) | 95.2 | 0.29 | 0.33 | 0.51 |
| Ex. 10 | 49.5 mole % | 0.56 | $Al^{3+}$ (96.6) | 95.2 | 0.29 | 0.33 | 0.51 |
| Ex. 11 | 49.5 mole % | 0.56 | $Al^{3+}$ (77.3)/$La^{3+}$ (25.1) | 95.2 | 0.31 | 0.31 | 0.55 |
| Ex. 12 | 60.1 mole % | 0.49 | $Al^{3+}$ (77.3)/$La^{3+}$ (25.1) | 95.2 | 0.31 | 0.31 | 0.63 |
| Ex. 13 | 49.5 mole % | 0.56 | $Al^{3+}$ (41)/$La^{3+}$ (4)/$Ca^{2+}$ (10) | 113.6 | 0.15 | 0.75 | 0.27 |
| Ex. 14 | 49.5 mole % | 0.56 | $Al^{3+}$ (77)/$La^{3+}$ (6.6)/$Ca^{2+}$ (18.3) | 204.4 | 0.29 | 0.71 | 0.51 |
| Ex. 15 | 49.5 mole % | 0.56 | $Al^{3+}$ (41)/$La^{3+}$ (4)/$Ca^{2+}$ (10) | 113.6 | 0.15 | 0.75 | 0.27 |
| Ex. 16 | 49.5 mole % | 0.56 | $Al^{3+}$ (41)/$La^{3+}$ (4)/$Ca^{2+}$ (10) | 113.6 | 0.15 | 0.75 | 0.27 |
| Ex. 17 | 49.5 mole % | 0.56 | $Al^{3+}$ (77.3)/$La^{3+}$ (25.1) | 95.2 | 0.31 | 0.33 | 0.55 |
| Ex. 18 | 49.5 mole % | 0.56 | $Al^{3+}$ (77.3)/$La^{3+}$ (25.1) | 95.2 | 0.31 | 0.33 | 0.55 |
| Ex. 19 | 49.5 mole % | 0.56 | $Al^{3+}$ (77.3)/$La^{3+}$ (25.1) | 95.2 | 0.31 | 0.33 | 0.55 |
| Ex. 20 | 49.5 mole % | 0.56 | $Al^{3+}$ (77.3)/$La^{3+}$ (25.1) | 95.2 | 0.31 | 0.33 | 0.55 |
| Ex. 21 | 49.5 mole % | 0.56 | $Al^{3+}$ (77.3)/$La^{3+}$ (25.1) | 95.2 | 0.31 | 0.33 | 0.55 |
| Ex. 22 | 37.6 mole % | 0.55 | $Al^{3+}$ (77.3)/$La^{3+}$ (25.1) | 95.2 | 0.31 | 0.31 | 0.56 |

(*1): Mole % of hydrogenphosphoric diester monomer in component (A)
(*2): Amount of fluoride ions/mmols

TABLE 3

| | Adhesion to tooth/Mpa (standard deviation) | | Storage stability | |
|---|---|---|---|---|
| | Enamel | Dentin | Salt precipitation | Gelling property |
| Ex. 1 | 15.2(3.1) | 15.8(1.9) | ◎ | ◎ |
| Ex. 2 | 15.0(1.9) | 15.9(2.2) | ◎ | ◎ |
| Ex. 3 | 16.8(1.8) | 17.8(3.1) | ◎ | ◎ |
| Ex. 4 | 12.2(1.3) | 13.3(2.2) | ◎ | ◎ |
| Ex. 5 | 13.3(2.1) | 13.9(1.1) | ◎ | ○(*1) |
| Ex. 6 | 15.5(2.2) | 15.2(1.9) | ○(*2) | ◎ |
| Ex. 7 | 12.2(1.7) | 13.0(2.1) | ◎ | ◎ |
| Ex. 8 | 19.8(2.3) | 15.8(3.4) | ◎ | ◎ |
| Ex. 9 | 21.8(2.0) | 24.5(3.1) | ◎ | ◎ |
| Ex. 10 | 22.8(3.2) | 23.9(2.5) | ◎ | ◎ |
| Ex. 11 | 23.7(3.1) | 26.8(2.7) | ◎ | ◎ |
| Ex. 12 | 22.8(3.0) | 23.8(4.1) | ◎ | ◎ |
| Ex. 13 | 22.5(2.2) | 23.2(1.2) | ◎ | ◎ |
| Ex. 14 | 20.9(2.9) | 24.9(3.3) | ◎ | ◎ |
| Ex. 15 | 24.5(2.2) | 26.2(1.2) | ◎ | ◎ |
| Ex. 16 | 22.9(2.9) | 25.9(3.3) | ◎ | ◎ |
| Ex. 17 | 14.2(2.7) | 15.8(2.9) | ◎ | ◎ |
| Ex. 18 | 13.2(1.9) | 14.3(1.5) | ◎ | ◎ |
| Ex. 19 | 17.4(2.2) | 15.7(3.2) | ◎ | ○(*3) |
| Ex. 20 | 14.2(2.1) | 14.9(2.2) | ◎ | ◎ |
| Ex. 21 | 17.9(2.2) | 18.2(2.4) | ◎ | ◎ |
| Ex. 22 | 14.8(1.9) | 15.0(2.0) | ◎ | ◎ |

(*1): 33 days after
(*2): 14 days after
(*3): 32 days

TABLE 4

| | Acidic monomer (A) | | | | | | |
|---|---|---|---|---|---|---|---|
| | (A-1) | | (A-2) | | | | (C) |
| | PM2 | 6PPH | PM1 | MAC-10 | (B')* | (E')* | Water |
| Comp. Ex. 1 | | | 100 | | Al(O-i-pr)3 (20) | FNa(4) | 76 |
| Comp. Ex. 2 | | | 100 | | Al(O-i-pr)3 (20) | | 76 |
| Comp. Ex. 3 | | | | 100 | Al(O-i-pr)3 (20) | FNa(4) | 76 |
| Comp. Ex. 4 | 30 | | 70 | | Al(O-i-pr)3 (20) | FNa(4) | 76 |
| Comp. Ex. 5 | 60 | | 40 | | | FNa(4) | 76 |
| Comp. Ex. 6 | 60 | | 40 | | Al(O-i-pr)3 (20) | | 76 |
| Comp. Ex. 7 | 60 | | 40 | | Al(O-i-pr)3 (20) | FNa(0.8) | 76 |
| Comp. Ex. 8 | 60 | | 40 | | Al(O-i-pr)3 (20) | FNa(27) | 76 |
| Comp. Ex. 9 | 60 | | 40 | | Al(O-i-pr)3 (20) | FNa(4) | 0 |
| Comp. Ex. 10 | 60 | | 60 | | Al(O-i-pr)3 (20) | FNa(4) | 76 |
| Comp. Ex. 11 | 60 | | 60 | | MF2 (40) | | 76 |
| Comp. Ex. 12 | 60 | | 40 | | MF3 (24) | | 76 |

| | (D) | (F) Non-acidic monomer | | | (G) |
|---|---|---|---|---|---|
| | Solvent | BisGMA | 3G | HEMA | Initiator |
| Comp. Ex. 1 | IPA(340) | 120 | 80 | 100 | CQ(4.0), DMBE(4.0) |
| Comp. Ex. 2 | IPA(340) | 120 | 80 | 100 | CQ(4.0), DMBE(4.0) |
| Comp. Ex. 3 | IPA(340) | 120 | 80 | 100 | CQ(4.0), DMBE(4.0) |

TABLE 4-continued

| | | | | | |
|---|---|---|---|---|---|
| Comp. Ex. 4 | IPA(340) | 120 | 80 | 100 | CQ(4.0), DMBE(4.0) |
| Comp. Ex. 5 | IPA(340) | 120 | 80 | 100 | CQ(4.0), DMBE(4.0) |
| Comp. Ex. 6 | IPA(340) | 120 | 80 | 100 | CQ(4.0), DMBE(4.0) |
| Comp. Ex. 7 | IPA(340) | 120 | 80 | 100 | CQ(4.0), DMBE(4.0) |
| Comp. Ex. 8 | IPA(340) | 120 | 80 | 100 | CQ(4.0), DMBE(4.0) |
| Comp. Ex. 9 | IPA(340) | 120 | 80 | 100 | CQ(4.0), DMBE(4.0) |
| Comp. Ex. 10 | | 120 | 80 | 100 | CQ(4.0), DMBE(4.0) |
| Comp. Ex. 11 | IPA(340) | 120 | 80 | 100 | CQ(4.0), DMBE(4.0) |
| Comp. Ex. 12 | IPA(340) | 120 | 80 | 100 | CQ(4.0), DMBE(4.0) |

*(B'): Polyvalent metal ion-releasing component, (E'): Fluoride ion-releasing component.

TABLE 5

| | (*1) | $TV_A$ | Amount of polyvalent metal ions/mmols | (*2) | $TV_P$ | $R_F$ ($V_F/TV_P$) | $R_P$ ($TV_P/TV_A$) |
|---|---|---|---|---|---|---|---|
| Comp. Ex. 1 | 0 mole % | 0.48 | $Al^{3+}$ (96.6) | 95.2 | 0.29 | 0.33 | 0.61 |
| Comp. Ex. 2 | 0 mole % | 0.48 | $Al^{3+}$ (96.6) | 0 | 0.29 | — | 0.61 |
| Comp. Ex. 3 | 0 mole % | 0.31 | $Al^{3+}$ (96.6) | 95.2 | 0.29 | 0.33 | 0.95 |
| Comp. Ex. 4 | 21.8 mole % | 0.52 | $Al^{3+}$ (96.6) | 95.2 | 0.29 | 0.33 | 0.56 |
| Comp. Ex. 5 | 49.5 mole % | 0.56 | 0 | 95.2 | — | — | — |
| Comp. Ex. 6 | 49.5 mole % | 0.56 | $Al^{3+}$ (96.6) | 0 | 0.29 | — | 0.51 |
| Comp. Ex. 7 | 49.5 mole % | 0.56 | $Al^{3+}$ (96.6) | 19 | 0.29 | 0.07 | 0.51 |
| Comp. Ex. 8 | 49.5 mole % | 0.56 | $Al^{3+}$ (96.6) | 643 | 0.29 | 2.22 | 0.51 |
| Comp. Ex. 9 | 49.5 mole % | 0.56 | $Al^{3+}$ (0) | 95.2 | — | — | 0.51 |
| Comp. Ex. 10 | 49.5 mole % | 0.56 | $Al^{3+}$ (96.6) | 95.2 | 0.29 | 0.33 | 0.51 |
| Comp. Ex. 11 | 49.5 mole % | 0.56 | $Al^{3+}$ (35)/$La^{3+}$ (2.4)/$Ca^{2+}$ (5.8) | 21.5 | 0.12 | 0.17 | 0.22 |
| Comp. Ex. 12 | 49.5 mole % | 0.56 | $Al^{3+}$ (209)/$La^{3+}$ (14.5)/$Ca^{2+}$ (34.9) | 10.7 | 0.74 | 0.01 | 1.32 |

(*1): Mole % of hydrogenphosphoric diester monomer in component (A)
(*2): Amount of fluoride ions/mmols

TABLE 6

| | Adhesion to tooth/Mpa (standard deviation) | | Storage stability | |
|---|---|---|---|---|
| | Enamel | Dentin | Salt precipitation | Gelling property |
| Comp. Ex. 1 | 8.8(1.0) | 9.2(2.2) | ◎ | ◎ |
| Comp. Ex. 2 | 9.4(1.0) | 10.3(1.9) | ◎ | ◎ |
| Comp. Ex. 3 | 7.2(1.0) | 8.1(1.2) | ◎ | ◎ |
| Comp. Ex. 4 | 9.3(1.8) | 9.6(2.0) | ◎ | ◎ |
| Comp. Ex. 5 | 3.0(1.9) | 3.8(1.1) | ◎ | ◎ |
| Comp. Ex. 6 | 16.8(2.1) | 16.9(3.1) | X | ◎ |
| Comp. Ex. 7 | 14.2(3.2) | 14.7(2.8) | X | ◎ |
| Comp. Ex. 8 | 7.2(2.4) | 9.2(3.1) | ◎ | ◎ |
| Comp. Ex. 9 | 2.1(0.8) | 3.2(1.0) | — | — |
| Comp. Ex. 10 | 5.9(2.0) | 4.6(2.1) | X | X (1 day) |
| Comp. Ex. 11 | 21.2(3.2) | 21.6(1.7) | X | ◎ |
| Comp. Ex. 12 | 20.1(1.9) | 22.7(2.3) | X | ◎ |

The dental adhesives of Examples 1 to 22 of the present invention all exhibit favorable results concerning the adhesion to the enamel and to the dentin, and the salt precipitation and gelling property.

The dental adhesives of Comparative Examples 1 to 3, on the other hand, do not contain hydrogenphosphoric dieter component (A-1) as the acidic group-containing polymerizable monomer (A) but contain the other acidic group-containing polymerizable monomers (A-2) only. Though the salt precipitation and gelling property are suppressed, the adhesion to the tooth is low probably because of insufficient ionic crosslinking between the polyvalent metal ions (B) and the other acidic group-containing polymerizable monomer (A-2) and insufficient formation of the crosslinked structure in the cured body. Comparative Example 2 is a case where no fluoride ion (E) is added. In this case, the salt precipitation has also been favorably suppressed and from which it is confirmed that the salt precipitation is a problem that specifically occurs when the hydrogenphosphoric diester monomer (A-1) is used as the acidic group-containing polymerizable monomer (A).

Comparative Example 4 is a case where the amount of the hydrogenphosphoric diester monomer (A-1) is not satisfying the requirement of the invention, and the adhesion to the tooth is insufficient.

Comparative Example 5 is a case where the polyvalent metal ions (B) are not quite contained without attaining the effect for improving the adhesion by ionic crosslinking, and the adhesion to the tooth is greatly lowered.

Comparative Example 6 is a case where fluoride ions (E) are not quite contained precipitating, in a large amount, the salt of the acidic group-containing polymerizable monomer and polyvalent metal ions, and the adhesion to the tooth is small.

Comparative Examples 7 and 8 are not containing the fluoride ions (E) in such amounts that the valence number ratio ($R_F$) lies in the predetermined range (0.2 to 2.0). For example, Comparative Example 7 is not containing fluoride ions (E) in a sufficient amount without, therefore, suppressing the formation of a salt of the acidic group-containing polymerizable monomer (A) and polyvalent metal ions (B), and exhibiting a small adhering strength to the tooth. Comparative Example 8, on the other hand, contains fluoride ions (E) in a too large amount in which case the polyvalent metal ions (B) are not ionically bonded to the acidic group-containing polymerizable monomer (A) smoothly, and the adhering strength to the tooth is small, too.

Comparative Example 9 is a case where water (C) is not quite contained. In this case, however, the polyvalent metal ions (B) are not eluted out, and the effect for improving the adhesion is not quite obtained.

Comparative Example 10 is a case where the water-soluble organic solvent (D) is not quite contained. In this case, the applicability of the solution lowers due to an increased viscosity, and the adhesion to the tooth tends to decrease. Besides, the salt precipitates and the liquid is gelled.

Comparative Example 11 is a case of using the multi-ion-releasing component (B' E') MF2 treated with the acid for 40 minutes [the multi-ion-releasing component (B'E') MF1 used in Examples 13 to 16 was the component treated with the acid for 15 minutes] as the source of polyvalent metal ions (B) and fluoride ions (E). In this case, the fluoride ions (E) have been removed a lot due to the treatment with the acid for an extended period of time and, therefore, the fluoride ions are eluted out in a small amount making it difficult to satisfy the requirement of the invention in that the valence number ratio ($R_F$) lies in the predetermined range (0.2 to 2.0). Therefore, formation of the salt of the acidic group-containing polymerizable monomer (A) and polyvalent metal ions (B) is not suppressed, and the salt precipitates in the adhesive that is obtained.

Comparative Example 12 is a case where the multi-ion-releasing component (B'E') MF3 without treated with the acid is used as the source of polyvalent metal ions (B) and fluoride ions (E). In this case, however, the fluoride ions are eluted out at a very small rate or are not almost eluted out, and the requirement of the invention is not satisfied, i.e., the valence number ratio ($R_F$) does not lie in the predetermined range (0.2 to 2.0). Therefore, the salt precipitates in the adhesive that is obtained.

The invention claimed is:

1. A dental adhesive composition which is acidic and contains an acidic group-containing polymerizable monomer (A), polyvalent metal ions (B), water (C), a water-soluble organic solvent (D) and fluoride ions (E), wherein
   said acidic group-containing polymerizable monomer (A) includes 40 to 60% by mole of a phosphoric acid-type compound having a hydrogenphosphoric diester group (A-1); and
   the contents of said fluoride ions (E) and said polyvalent metal ions (B) are so set that a valence number ratio ($R_F$) defined by the following formula (1):

$$R_F = V_F/TV_P \quad (1)$$

wherein,
   $V_F$ is a valence number of the fluoride ions (E) contained in the composition, and
   $TV_P$ is a total valence number of the polyvalent metal ions (B) contained in the composition,
satisfies a range of 0.3 to 1.0.

2. The dental adhesive composition according to claim 1, wherein the contents of said polyvalent metal ions (B) and said acidic group-containing polymerizable monomer (A) are so set that the valence number ratio ($R_P$) defined by the following formula (2):

$$R_P = TV_P/TV_A \quad (2)$$

wherein,
   $TV_P$ is a total valence number of the polyvalent metal ions (B) contained in the composition, and
   $TV_A$ is a total valence number of the acidic groups possessed by the acidic group-containing polymerizable monomer (A) contained in the composition,
satisfies a range of 0.1 to 1.5.

3. The dental adhesive composition according to claim 1, wherein said phosphoric acid-type compound having said hydrogenphosphoric diester group is a bis[2-(meth)acryloyloxyethyl] hydrogenphosphate.

4. The dental adhesive composition according to claim 3, wherein said acidic group-containing polymerizable monomer (A) is partly a phosphoric acid-type compound having a dihydrogenphosphoric monoester group.

5. The dental adhesive composition according to claim 4, wherein said phosphoric acid-type compound having said dihydrogenphosphoric monoester group is a 2-(meth)acryloyloxyethyl dihydrogenphosphate.

6. The dental adhesive composition according to claim 1, further containing a non-acidic polymerizable monomer (F) which has no acidic group.

7. The dental adhesive composition according to claim 1, wherein the content of water (C) is 10 to 120 parts by mass per 100 parts by mass of the acidic group-containing polymerizable monomer (A).

8. The dental adhesive composition according to claim 1, wherein the content of the water-soluble organic solvent (D) is 100 to 600 parts by mass per 100 parts by mass of the acidic group-containing polymerizable monomer (A).

9. The dental adhesive composition according to claim 1, wherein the content of the non-acidic polymerizable monomer (F) is not more than 500 parts by mass per 100 parts by mass of the acidic group-containing polymerizable monomer (A).

10. The dental adhesive composition according to claim 1, which further, contains an effective amount of a photopolymerization initiator (G), and is used as a dental adhesive.

11. The dental adhesive composition according to claim 1, which is used as a tooth-pretreating material prior to applying the dental adhesive.

12. A method of producing a dental adhesive composition which contains an acidic group-containing polymerizable monomer (A), polyvalent metal ions (B), water (C), a water-soluble organic solvent (D) and fluoride ions (E), comprising:
   using a phosphoric acid-type compound having a hydrogenphosphoric diester group (A-1) of said acidic group-containing polymerizable monomer (A), said acidic group-containing polymerizable monomer (A) including 40 to 60% by mole of said phosphoric acid-type compound (A-1);
   using a polyvalent metal ion-releasing component (B') as a source of said polyvalent metal ions (B);
   using a fluoride ion-releasing component (E') as a source of said fluoride ions (E);
   mixing the acidic group-containing polymerizable monomer (A), polyvalent metal ion-releasing component (B'), water (C), water-soluble organic solvent (D) and fluoride ion-releasing component (E') together, and ripening the mixture so that the polyvalent metal ions and the fluoride ions released from said polyvalent metal ion-releasing component (B') and said fluoride ion-releasing component (E') maintain a valence number ratio ($R_F$) represented by the following formula (1), $$R_F = V_F/TV_P \tag{1}$$

wherein,
  $V_F$ is a valence number of the fluoride ions (E) contained in the composition, and
  $TV_p$ is a total valence number of the polyvalent metal ions (B) contained in the composition, that lies a range of 0.3 to 1.0.

13. The method of producing a dental adhesive composition according to claim 12, wherein either said polyvalent metal ion-releasing component (B') or said fluoride ion-releasing component (E') is a multi-ion-releasing component (B'E') which releases the polyvalent metal ions and the fluoride ions.

* * * * *